(12) United States Patent
Maruyama

(10) Patent No.: US 12,734,340 B2
(45) Date of Patent: Sep. 15, 2026

(54) GUIDE WIRE AND METHOD OF MANUFACTURING GUIDE WIRE

(71) Applicant: TERUMO KABUSHIKI KAISHA, Tokyo (JP)

(72) Inventor: Akihiro Maruyama, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 538 days.

(21) Appl. No.: 18/307,514

(22) Filed: Apr. 26, 2023

(65) Prior Publication Data

US 2023/0302260 A1 Sep. 28, 2023

Related U.S. Application Data

(63) Continuation of application No. PCT/JP2021/039235, filed on Oct. 25, 2021.

(30) Foreign Application Priority Data

Oct. 30, 2020 (JP) ................................ 2020-183259

(51) Int. Cl.
*A61M 25/09* (2006.01)

(52) U.S. Cl.
CPC ... *A61M 25/09* (2013.01); *A61M 2025/09108* (2013.01); *A61M 2025/09158* (2013.01); *A61M 2025/09175* (2013.01)

(58) Field of Classification Search
CPC ........ A61M 25/09; A61M 2025/09108; A61M 2025/09158; A61M 2025/09175; A61M 2025/09133
See application file for complete search history.

(56) References Cited

U.S. PATENT DOCUMENTS 5,238,004 A 8/1993 Sahatjian et al.
5,980,471 A * 11/1999 Jafari .................... A61M 25/09 600/585

(Continued)

FOREIGN PATENT DOCUMENTS

EP 1142604 A1 * 10/2001 ............ A61M 25/09
JP H05508559 A 12/1993

(Continued)

OTHER PUBLICATIONS

International Search Report (PCT/ISA/210) with translation and Written Opinion (PCT/ISA/237) mailed on Dec. 28, 2021, by the Japanese Patent Office as the International Searching Authority for International Application No. PCT/JP2021/039235. (10 pages).

(Continued)

*Primary Examiner* — Jeffrey G. Hoekstra
(74) *Attorney, Agent, or Firm* — Buchanan Ingersoll & Rooney PC

(57) ABSTRACT

A guide wire having a shaping property capable of shaping into a desired shape and a shape retaining property of retaining a shape at a time of shaping against an external force applied in a blood vessel, thereby allowing a procedure to be easily performed while maintaining high operability and blood vessel selectivity; and a method of manufacturing a guide wire. The guide wire includes an elongated core component including a flat portion at a distal end of the elongated core component. The flat portion is formed of a Ni—Ti alloy having an elastic portion of total indentation work of 46.0% to 59.5% and having a Martens hardness of 1300 $N/mm^2$ to 3000 $N/mm^2$, more preferably having a Martens hardness of 1300 $N/mm^2$ to 2120 $N/mm^2$.

20 Claims, 15 Drawing Sheets

(56) References Cited

U.S. PATENT DOCUMENTS

| | | | | |
|---|---|---|---|---|
| 6,190,332 | B1 | 2/2001 | Muni et al. | |
| 6,375,629 | B1 | 4/2002 | Muni et al. | |
| 6,478,752 | B1 | 11/2002 | Ishikawa et al. | |
| 7,153,277 | B2 * | 12/2006 | Skujins | A61M 25/09 600/585 |
| 7,618,379 | B2 * | 11/2009 | Reynolds | A61L 31/022 604/524 |
| 7,785,273 | B2 * | 8/2010 | Eskuri | A61M 25/09 600/585 |
| 7,922,673 | B2 * | 4/2011 | Murayama | A61M 25/09 600/585 |
| 8,728,010 | B2 * | 5/2014 | Hirshman | A61M 25/0041 600/585 |
| 10,335,580 | B2 * | 7/2019 | Chludzinski | B21F 45/008 |
| 11,806,488 | B2 * | 11/2023 | Purtzer | B23K 35/3006 |
| 2011/0015618 | A1 * | 1/2011 | Satou | A61M 25/09016 604/528 |
| 2013/0006149 | A1 | 1/2013 | Purtzer | |
| 2016/0327877 | A1 | 11/2016 | Kurimoto et al. | |
| 2017/0333683 | A1 * | 11/2017 | Purtzer | C22F 1/10 |
| 2020/0405920 | A1 | 12/2020 | Matsushita et al. | |

FOREIGN PATENT DOCUMENTS

| | | | | |
|---|---|---|---|---|
| JP | 2001009041 | A | 1/2001 | |
| JP | 2002503529 | A | 2/2002 | |
| JP | 2006501926 | A | 1/2006 | |
| JP | 2016212400 | A | 12/2016 | |
| JP | 2017205557 | A | 11/2017 | |
| WO | 9115152 | A1 | 10/1991 | |
| WO | 0035528 | A1 | 6/2000 | |
| WO | 2004033016 | A1 | 4/2004 | |
| WO | 2019176345 | A1 | 9/2019 | |
| WO | WO-2021038845 | A1 * | 3/2021 | A61M 25/09016 |

OTHER PUBLICATIONS

Extended European Search Report dated Mar. 5, 2024, issued in corresponding European Application No. 21886119.3. (5 pages).

English Translations of the International Search Report (Form PCT/ISA/210) and the Written Opinion of the International Searching Authority (Form PCT/ISA/237) issued Dec. 28, 2021, by the Japan Patent Office in corresponding International Application No. PCT/JP2021/039235. (6 pages).

* cited by examiner

FIG. 8

Table 1

| Example number | Manufacture conditions | | | | | Average of elastic portion of total indentation work (%) | Average of Martens hardness (N/mm²) |
|---|---|---|---|---|---|---|---|
| | Thickness of flat portion (μm) | Flat portion (mm) | Flat portion + transition portion (mm) | Heat treatment length (mm) | Heat treatment ratio (%) | | |
| Example 1 | 27 | 9 | 16 | 12.5 | 50 | 53.8 | 2154 |
| Example 2 | 27 | 9 | 16 | 13.0 | 57 | 54.4 | 2694 |
| Example 3 | 27 | 9 | 16 | 13.8 | 69 | 50.4 | 2140 |
| Example 4 | 27 | 9 | 16 | 13.6 | 65 | 58.9 | 1557 |
| Example 5 | 27 | 9 | 16 | 12.8 | 54 | 59.4 | 1452 |
| Example 6 | 27 | 9 | 16 | 13.3 | 61 | 51.5 | 1827 |
| Example 7 | 32 | 13 | 16 | 13.6 | 20 | 49.8 | 2107 |
| Example 8 | 32 | 13 | 16 | 13.7 | 23 | 46.1 | 1818 |
| Example 9 | 27 | 9 | 16 | 7.2 | -26 | 58.9 | 1557 |
| Example 10 | 27 | 9 | 16 | 9.3 | 4 | 58.9 | 1557 |
| Example 11 | 27 | 9 | 16 | 10.3 | 19 | 58.9 | 1557 |
| Example 12 | 27 | 9 | 16 | 11.7 | 38 | 58.9 | 1557 |
| Example 13 | 27 | 9 | 16 | 14.4 | 77 | 58.9 | 1557 |
| Example 14 | 27 | 9 | 16 | 16.0 | 100 | 58.9 | 1557 |
| Example 15 | 27 | 9 | 16 | 18.9 | 141 | 58.9 | 1557 |
| Example 16 | 27 | 9 | 16 | 20.6 | 165 | 58.9 | 1557 |

FIG. 9

Table 2

| | Manufacture conditions | | | | | Average of elastic portion of total indentation work (%) | Average of Martens hardness ($N/mm^2$) |
|---|---|---|---|---|---|---|---|
| Example number | Thickness of flat portion (μm) | Flat portion (mm) | Flat portion + transition portion (mm) | Heat treatment length (mm) | Heat treatment ratio (%) | | |
| Comparative Example 1 | 27 | 9 | 16 | 0.0 | No heat treatment | 46.7 | 3007 |
| Comparative Example 2 | 27 | 9 | 16 | 13.7 | 67 | 60.1 | 806 |
| Comparative Example 3 | 32 | 13 | 16 | 14.3 | 43 | 45.3 | 1681 |
| Comparative Example 4 | 32 | 13 | 16 | 13.0 | 0 | 59.8 | 2207 |

FIG. 10

Table 3

| | Evaluation results | | | |
|---|---|---|---|---|
| Example number | Shaping property test | Shape retaining property test | Prolapse resistance test (maximum angle allowing insertion) | Kink resistance test |
| Example 1 | Fair | Good | Fair (110°) | Good |
| Example 2 | Fair | Good | ND | ND |
| Example 3 | Fair | Good | Fair (110°) | Good |
| Example 4 | Good | Good | Good (120°) | Good |
| Example 5 | Good | Good | ND | ND |
| Example 6 | Good | Good | Good (120°) | Good |
| Example 7 | Good | Good | Good (120°) | Good |
| Example 8 | Good | Good | Good (120°) | Good |
| Example 9 | Good | Good | Poor (90°) | Good |
| Example 10 | Good | Good | Poor (100°) | Good |
| Example 11 | Good | Good | Fair (110°) | Good |
| Example 12 | Good | Good | Fair (110°) | Good |
| Example 13 | Good | Good | Fair (110°) | Good |
| Example 14 | Good | Good | Fair (110°) | Good |
| Example 15 | Good | Good | Fair (110°) | Poor |
| Example 16 | Good | Good | Fair (110°) | Poor |

FIG. 11

Table 4

| | Evaluation results | | | |
|---|---|---|---|---|
| Example number | Shaping property test | Shape retaining property test | Prolapse resistance test (maximum angle allowing insertion) | Kink resistance test |
| Comparative Example 1 | Poor | Good | ND | ND |
| Comparative Example 2 | Good | Poor | Fair (110°) | Good |
| Comparative Example 3 | Good | Poor | Good (120°) | Good |
| Comparative Example 4 | Poor | Good | Fair (110°) | Good |

GUIDE WIRE AND METHOD OF MANUFACTURING GUIDE WIRE

CROSS-REFERENCES TO RELATED APPLICATIONS

This application is a continuation of International Application No. PCT/JP2021/039235 filed on Oct. 25, 2021, which claims priority to Japanese Application No. 2020-183259 filed on Oct. 30, 2020, the entire content of both of which is incorporated herein by reference.

TECHNOLOGICAL FIELD

The present disclosure generally relates to a guide wire and a method of manufacturing a guide wire.

BACKGROUND DISCUSSION

A guide wire is a medical device used to guide, to a stenosis occurring in a blood vessel such as a coronary artery, various types of catheters for treating the stenosis.

The guide wire travels through a complicated curved portion or branched portion of the blood vessel and pass through the stenosis. Therefore, a distal portion of the guide wire is required to have flexibility, restorability against an external force, and kink resistance. In order to satisfy these requirements, the distal portion of the guide wire can be formed of a super-elastic alloy such as a Ni—Ti alloy.

Incidentally, before inserting the guide wire into the blood vessel, an operator may give a desired shape (shaping) to the distal portion of the guide wire for a purpose of improving operability of the guide wire in the blood vessel and blood vessel selectivity at a branch portion. Therefore, it is preferable that the distal portion of the guide wire can be rather easily shaped. However, when a guide wire including a distal portion formed of a super-elastic alloy has high superelasticity, even the operator applies an external force for shaping, the guide wire is restored to a shape before shaping when the external force is removed, and it can be difficult for the operator to give the desired shape.

Japanese Patent Application Publication No. 2002-503529 A discloses a technique of subjecting a distal portion of a guide wire formed of a super-elastic alloy to cold working or heat treatment, thereby reducing superelasticity and enabling shaping of the distal portion of the guide wire.

However, when the superelasticity of the distal portion of the guide wire is excessively decreased, the shape of the guide wire can be difficult to restore, and thus a shape retaining property, which is a property of retaining a shape at a time of shaping, is decreased. The guide wire inserted into the blood vessel receives an external force when the distal portion comes into contact with a blood vessel wall or a stenosis. At this time, the guide wire including the distal portion having excessively decreased superelasticity is plastically deformed into a shape different from the shape at the time of shaping. Accordingly, the operability and the blood vessel selectivity of the guide wire are decreased. When the distal portion of the guide wire is plastically deformed during an operation in the blood vessel, the operator needs to remove the guide wire from the blood vessel to reshape the guide wire or replace the guide wire with another guide wire, which complicates a procedure. Accordingly, procedure time is extended, and burden on the operator and a patient is increased.

A magnitude of the external force applied to the guide wire in the blood vessel is smaller than that of the external force applied for shaping by the operator. Therefore, the distal portion of the guide wire needs to have a physical property capable of being deformed by a large force applied by the operator for shaping, and capable of restoring the shape at the time of shaping without being plastically deformed by a small force applied during a procedure. That is, the distal portion of the guide wire needs to have both a shaping property capable of shaping into a desired shape before being inserted into a blood vessel and a shape retaining property capable of retaining a shape at the time of shaping against an external force applied in the blood vessel.

SUMMARY

A guide wire is disclosed having a shaping property capable of shaping into a desired shape and a shape retaining property of retaining a shape at a time of shaping against an external force applied in a blood vessel, and a method of manufacturing a guide wire.

A guide wire according to the present embodiment includes: an elongated core component including a flat portion at a distal end of the elongated core component. The flat portion is made of a Ni—Ti alloy having an elastic portion of total indentation work of 46.0% to 59.5% and a Martens hardness of 1300 N/mm$^2$ to 3000 N/mm$^2$.

A guide wire according to the present disclosure includes: an elongated core component including a flat portion at a distal end of the elongated core component, the flat portion having an elastic portion of total indentation work of 46.0% to 59.5% and a Martens hardness of 1300 N/mm$^2$ to 3000 N/mm$^2$; and a tubular body that is spirally wound around a portion of the elongated core component.

A method of manufacturing the guide wire according to the present embodiment is a method of manufacturing a guide wire including a core component. The method includes: cold working a distal portion of the core component such that the distal portion includes a flat portion and a transition portion extending from a proximal end of the flat portion toward a proximal end side along a longitudinal direction; and heat treating the flat portion and at least a part of the transition portion such that an elastic portion of total indentation work of the flat portion is 46.0% to 59.5% and a Martens hardness of the flat portion is 1300 N/mm$^2$ to 3000 N/mm$^2$.

According to an embodiment of the disclosure, by controlling an elastic portion of total indentation work and a Martens hardness at a distal portion of a guide wire made of a Ni—Ti alloy within a predetermined range, it is possible to provide a guide wire having a physical property capable of being deformed by a large force applied by an operator for shaping, and capable of restoring a shape at a time of shaping without being plastically deformed by a small force applied during a procedure. That is, according to an embodiment of the disclosure, it is possible to provide a guide wire having both a shaping property and a shape retaining property. Accordingly, the guide wire can be shaped by an operator, and can be restored to a shape at a time of shaping even when an external force that can deform the distal portion is received in a blood vessel. Therefore, the guide wire can maintain relatively high operability and blood vessel selectivity given by shaping even during a procedure. Further, the operator does not need to remove the guide wire from the blood vessel and reshape the guide wire or replace the guide wire with another guide wire, and thus the procedure can be rather easily performed. Accordingly, the procedure time can be shortened, and thus the burden on the operator and the patient can be reduced.

BRIEF DESCRIPTION OF THE DRAWINGS

FIG. 8 is Table 1 illustrating manufacture conditions in Example 1 to Example 16.

FIG. 9 is Table 2 illustrating manufacture conditions in Comparative Example 1 to Comparative Example 4.

FIG. 10 is Table 3 illustrating evaluation results in Example 1 to Example 16.

FIG. 11 is Table 4 illustrating evaluation results in Comparative Example 1 to Comparative Example 4.

DETAILED DESCRIPTION

Figure 1:
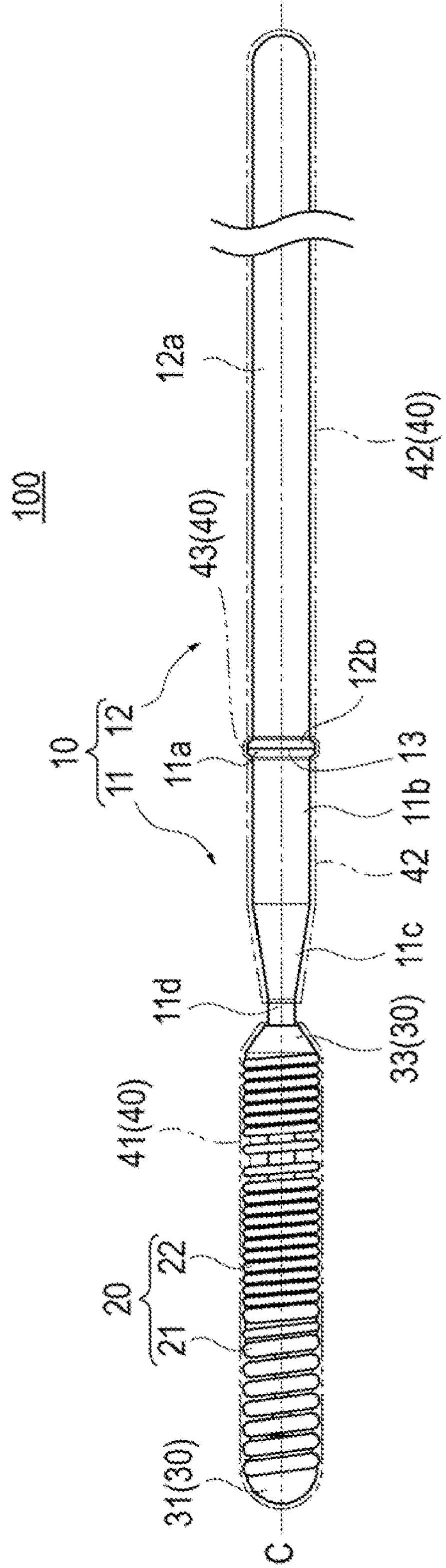
FIG. 1 is a schematic plan view of a guide wire according to the present embodiment.

Set forth below with reference to the accompanying drawings is a detailed description of embodiments of a guide wire and a method of manufacturing a guide wire.

Further, in the drawings attached to the present specification, for convenience of illustration and understanding, a scale, an aspect ratio, a shape, and the like may be changed from actual ones and may be schematically expressed as appropriate, and the drawings are just examples and do not limit the interpretation of the invention.

In the present specification, for convenience of description, directions in a case in which a guide wire 100 is in a natural state (a state where the guide wire 100 is extended straight without applying an external force) are defined. In FIG. 1, a "longitudinal direction" is a direction in which the guide wire 100 extends and is a direction along a central axis C of the guide wire 100 (a horizontal direction in FIG. 1). A "radial direction" is a direction away from or approaching a core member in a cross section orthogonal to axis (a transverse section) of the core member with the longitudinal direction of the guide wire 100 as a reference axis. A "circumferential direction" is a rotation direction with the longitudinal direction of the core member as the reference axis. A "thickness direction" is defined as a direction in which, when a distal end of the guide wire 100 includes a flat portion 11*g*, a short side of a rectangle in a traverse sectional view of the flat portion 11*g* extends (a depth direction in the drawing). A "width direction" is a direction in which, when the distal end of the guide wire 100 includes the flat portion 11*g*, a long side of the rectangle in the traverse sectional view of the flat portion 11*g* extends (a vertical direction in the drawing).

Further, a side on which the guide wire 100 is inserted into a blood vessel is referred to as a "distal end side", and a side opposite to the distal end side (a side gripped by an operator) is referred to as a "proximal end side". Further, a portion including a certain range from a distal end (a most distal end) along the longitudinal direction is referred to as a "distal portion", and a portion including a certain range from a proximal end (a most proximal end) along the longitudinal direction is referred to as a "proximal portion".

In the following description, in a case in which the description is given by adding an ordinal number such as "first" or "second", unless otherwise specified, it is used for convenience and does not define any order.

The guide wire 100 according to the present embodiment can be a medical device that is inserted into a blood vessel, for example, in order to guide, to a stenosis, a catheter or a stent for performing intravascular treatment. The guide wire 100 may be inserted into a living body lumen other than the blood vessel (for example, an artery, a ureter, a bile duct, a fallopian tube, and a hepatic duct) according to a treatment purpose.

Configuration

Figure 2:
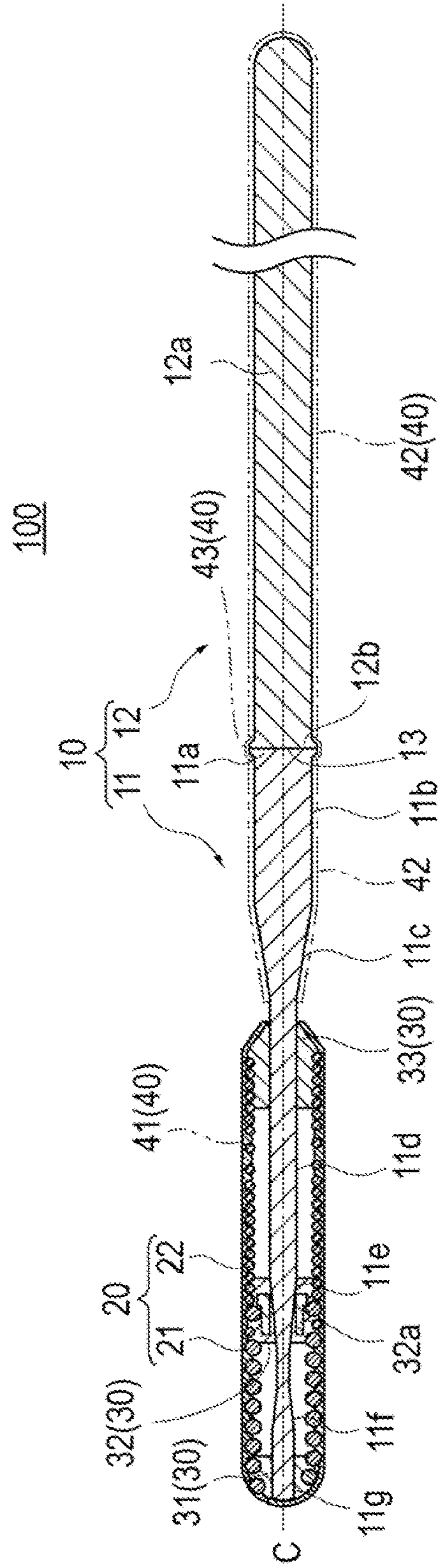
FIG. 2 is a partial cross-sectional view in a longitudinal direction when the guide wire according to the present embodiment is viewed in a thickness direction.

As illustrated in FIG. 1 or FIG. 2, the guide wire 100 according to the present embodiment includes an elongated core component 10, a tubular body 20 that covers a periphery of a distal portion of the core component 10, a fixing portion 30 that fixes the tubular body 20 to the core component 10, and a cover layer 40 that covers each member including the core component 10. Hereinafter, each part of the guide wire 100 will be described in detail.

Core Component

The core component 10 includes a first core member 11 and a second core member 12 disposed on a proximal end side of the first core member 11 and bonded to the first core member 11.

The first core member 11 is an elongated member extending from a distal end of the second core member 12 to the distal end side of the guide wire 100 along the longitudinal direction. The first core member 11 includes a first bonding portion 11*a*, a first constant outer diameter portion 11*b*, a first tapered portion 11*c*, a second constant outer diameter portion 11*d*, a second tapered portion 11*e*, a transition portion 11*f*, and a flat portion 11*g* in this order from a proximal end of the first core member 11 toward a distal end side of the first core member 11. Each part is integrally formed with each other.

The first bonding portion 11*a* is a portion bonded to a second bonding portion 12*b* of the second core member 12 described later. An outer diameter of the first bonding portion 11*a* is larger than an outer diameter of the first constant outer diameter portion 11*b* and is substantially equal to an outer diameter of the second bonding portion 12*b*. The outer diameter of the first bonding portion 11*a* and the outer diameter of the second bonding portion 12*b* are larger than the outer diameter of the first constant outer diameter portion 11*b* and an outer diameter of a proximal portion 12*a* of the second core member 12. That is, an area of a bonding surface 13 between the first bonding portion 11*a* and the second bonding portion 12*b* is larger than an area in cross section of the first constant outer diameter portion 11*b* of the first core member 11 and an area in cross section the proximal portion 12*a* of the second core member 12. Accordingly, a stress acting on the bonding surface 13 when the guide wire 100 is bent is dispersed to the first constant outer diameter portion 11*b* and the proximal portion 12*a*, which have an outer diameter smaller than that of the bonding surface 13, and it is possible to help prevent the stress from concentrating on the bonding surface 13. Accordingly, the core component 10 has relatively high bonding strength at the bonding surface 13.

The first constant outer diameter portion 11*b* extends by a predetermined length from a distal end of the first bonding portion 11*a* to a proximal end of the first tapered portion 11*c*. The outer diameter of the first constant outer diameter portion 11*b* is substantially constant, and is substantially equal to the outer diameter of the proximal portion 12*a* of the second core member 12.

The first tapered portion 11*c* extends by a predetermined length from a distal end of the first constant outer diameter portion 11*b* to a proximal end of the second constant outer diameter portion 11*d*. The first tapered portion 11*c* has a tapered shape whose outer diameter gradually decreases from the first constant outer diameter portion 11*b* toward the distal end side. The tapered shape of the first tapered portion 11*c* can be formed, for example, by subjecting the first core member 11 to mechanical grinding using a grindstone or etching using an acid.

The second constant outer diameter portion 11*d* extends by a predetermined length from a distal end of the first tapered portion 11*c* to a proximal end of the second tapered portion 11*e*. An outer diameter of the second constant outer diameter portion 11*d* is substantially constant and is smaller than the outer diameter of the first constant outer diameter portion 11*b*.

The second tapered portion 11*e* extends by a predetermined length from a distal end of the second constant outer diameter portion 11*d* to a proximal end of the transition portion 11*f*. The second tapered portion 11*e* has a tapered shape whose outer diameter gradually decreases from the second constant outer diameter portion 11*d* toward the transition portion 11*f*. The tapered shape of the second tapered portion 11*e* can be formed, for example, by subjecting the first core member 11 to mechanical grinding using a grindstone or etching using an acid.

Figure 3A:
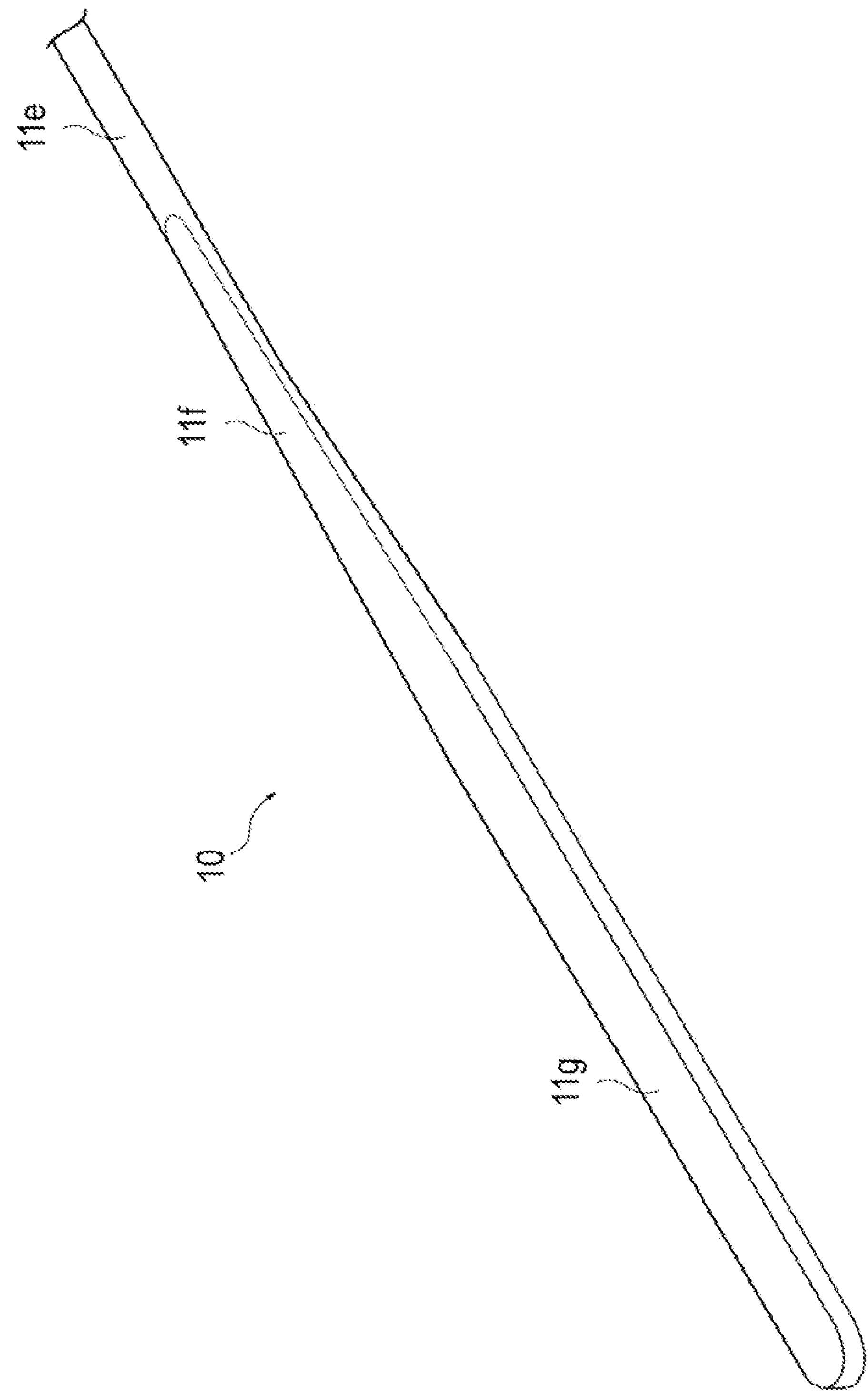
FIG. 3A is a schematic perspective view of a distal portion of a first core member of the guide wire according to the present embodiment.
Figure 3B:
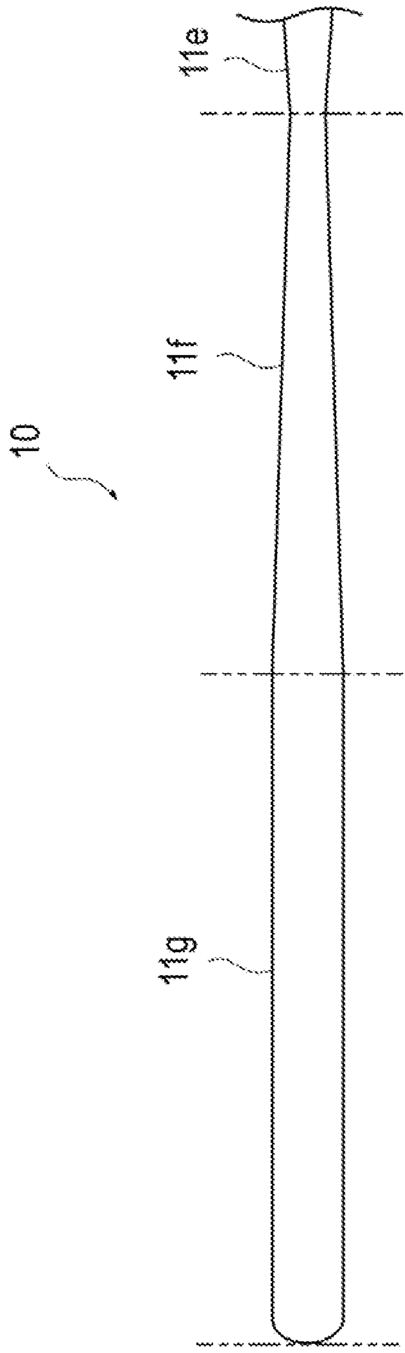
FIG. 3B is a schematic plan view of the distal portion of the first core member of the guide wire according to the present embodiment.

The transition portion 11*f* extends a predetermined length from a distal end of the second tapered portion 11*e* to a proximal end of the flat portion 11*g*. As illustrated in FIG. 3A or FIG. 3B, the transition portion 11*f* has a wedge shape whose thickness gradually decreases from the second tapered portion 11*e* toward the flat portion 11*g* and whose width gradually increases from the second tapered portion 11*e* toward the flat portion 11*g*. The wedge shape of the transition portion 11*f* can be formed, for example, by pressing the first core member 11 having a circular traverse sectional shape. The pressing is, for example, a type of cold working. The traverse sectional shape of the transition portion 11*f* in a plan view orthogonal to the longitudinal direction (traverse sectional view) is a circular shape having an outer diameter substantially equal to that of the second tapered portion 11*e* on the proximal end side, but is gradually deformed from the circular shape to a rectangular shape from the proximal end side toward the distal end side, and is a rectangular shape substantially the same as that of the flat portion 11*g* on the distal end side. A distal portion of the transition portion 11*f* has substantially the same thickness and width as a proximal portion of the flat portion 11*g*, and forms a surface continuous with the flat portion 11*g*. Two-dot chain lines in FIG. 3B are imaginary lines that partition regions of the flat portion 11*g*, the transition portion 11*f*, and the second tapered portion 11*e*. Further, the "thickness" of the flat portion 11*g* is a length of a short side of the rectangle in the traverse sectional view of the flat portion 11*g*, and the "width" of the flat portion 11*g* is a length of a long side of the rectangle in the traverse sectional view of the flat portion 11*g*.

The flat portion 11*g* extends by a predetermined length from a distal end of the transition portion 11*f* to the distal end of the guide wire 100. The flat portion 11*g* can be, for example, formed by pressing the first core member 11 having a circular traverse sectional shape. Accordingly, the flat portion 11*g* has a rectangular traverse sectional shape. The thickness of the flat portion 11*g* is substantially constant from the distal end of the transition portion 11*f* to a distal end of the flat portion 11*g*. As illustrated in FIGS. 3A and 3B, a shape of the flat portion 11*g* as viewed in the thickness direction is formed in a rectangular shape rounded at the distal end of the flat portion 11*g*. Accordingly, the width of the flat portion 11*g* is substantially constant from the distal end of the transition portion 11*f* toward the distal end side, and is smaller at the rounded portion at the distal end of the flat portion 11*g*. The width of the flat portion 11*g* may be constant from the distal end of the transition portion 11*f* to the distal end of the flat portion 11*g*. The traverse sectional shape of the flat portion 11*g* is not limited to a rectangular shape, and may be a rounded rectangular shape with R-shaped corners (or round-shaped corners).

A structure of the first core member 11 is not limited to the above. For example, the first core member 11 may have a constant outer shape or a constant outer diameter from a distal end to the proximal end of the first core member 11.

Further, in the first core member 11, at least a region where the flat portion 11*g* is located (preferably, the flat portion 11*g* and at least a part of the transition portion 11*f*) has both a shaping property and a shape retaining property.

The second core member 12 is an elongated member extending from the proximal end of the first core member 11 to the proximal end side of the guide wire 100. The second core member 12 includes the proximal portion 12*a* and the second bonding portion 12*b* in this order from a proximal end toward a distal end side of the second core member 12. Each part is integrally formed with each other.

The proximal portion 12*a* extends a predetermined length from a proximal end of the second bonding portion 12*b* toward the proximal end side of the guide wire 100. The outer diameter of the proximal portion 12*a* is substantially constant, and is substantially equal to the outer diameter of the first constant outer diameter portion 11*b*.

The second bonding portion 12*b* is a portion bonded to the first bonding portion 11*a*. The outer diameter of the second bonding portion 12*b* is larger than the outer diameter of the proximal portion 12*a* and equal to the outer diameter of the first bonding portion 11*a*. The first bonding portion 11*a* and the second bonding portion 12*b* can be bonded, for example, by welding, brazing, or soldering.

Here, a dimension example of the guide wire 100 will be described. An entire length of the guide wire 100 in the longitudinal direction can be, for example, 1000 mm to 4500 mm. A length of the first core member 11 can be, for example, 150 mm to 1000 mm. A total length of the first bonding portion 11*a* and the first constant outer diameter portion 11*b* can be, for example, 10 mm to 300 mm. A length of the first tapered portion 11*c* can be, for example, 10 mm to 100 mm. A length of the second constant outer diameter portion 11*d* can be, for example, 10 mm to 300 mm. A length of the second tapered portion 11*e* can be, for example, 10 mm to 100 mm. A length of the transition portion 11*f* can be, for example, 1 mm to 20 mm. A length of the flat portion 11*g* can be, for example, 1 mm to 20 mm.

The outer diameters of the first bonding portion 11*a* and the first constant outer diameter portion 11*b* can be, for example, 0.2 mm to 1 mm. The outer diameters of the first tapered portion 11*c* and the second constant outer diameter portion 11*d* can be, for example, 0.1 mm to 1 mm. The outer diameter of the second tapered portion 11*e* can be, for example, 0.05 mm to 1 mm. The thickness of the transition portion 11*f* can be, for example, 0.01 mm to 1 mm and the width of the transition portion 11*f* can be, for example, 0.05 mm to 1 mm. The thickness of the flat portion 11*g* can be, for example, 0.01 mm to 1 mm and the width of the flat portion 11*g* can be, for example, 0.05 mm to 1 mm.

A length of the second core member 12 can be, for example, 850 mm to 3500 mm. An outer diameter of the second core member 12 can be, for example, 0.2 mm to 1 mm.

The first core member 11 and the second core member 12 can be formed of various metal materials such as a super-elastic alloy such as Ni—Ti-based alloy, stainless steel such as SUS302, SUS304, SUS303, SUS316, SUS316L, SUS316J1, SUS316J1L, SUS405, SUS430, SUS434, SUS444, SUS429, and SUS430F, a piano wire, and a cobalt-based alloy. Further, the first core member 11 is preferably formed of a material having a lower rigidity than that of a material of the second core member 12. For example, the first core member 11 is formed of a Ni—Ti-based alloy, and the second core member 12 is formed of a stainless steel. The materials forming the first core member 11 and the second core member 12 are not limited to the above examples. Further, the first core member 11 and the second core member 12 may be formed of the same material.

Further, the core component 10 may be formed from a single continuous member instead of being formed from a plurality of members such as the first core member 11 and the second core member 12.

Tubular Body

The tubular body 20 is a member formed by spirally winding a wire member around the core component 10. In the present embodiment, the tubular body 20 is formed from a first coil 21 and a second coil 22 disposed on a proximal end side of the first coil 21. The first coil 21 is disposed from the distal end to an intermediate portion of the first core member 11. The second coil 22 is disposed from the intermediate portion to the proximal end side of the first core member 11. The tubular body 20 may be formed of a single coil. The tubular body 20 may be, for example, formed of three or more coils.

The first coil 21 surrounds the first core member 11 of the core component 10 and is fixed to the first core member 11. The first coil 21 is coaxially disposed with the first core member 11. A length of the first coil 21 can be, for example, 3 mm to 60 mm.

The first coil 21 is formed by spirally winding the wire member such that a gap is provided between adjacent wire members. The gaps between the adjacent wire members of the first coil 21 can be, for example, 1 μm to 10 μm. The gaps between the adjacent wire members of the first coil 21 are preferably equal.

The second coil 22 surrounds the first core member 11 of the core component 10 and is fixed to the first core member 11. The second coil 22 is coaxially disposed with the first core member 11. A length of the second coil 22 can be, for example, 10 mm to 400 mm.

The second coil 22 includes a densely wound portion in which the wire member is wound spirally and densely such that no gaps are provided between the adjacent wire members, and a sparsely wound portion in which the wire member is wound spirally and sparsely such that a gap is provided between the adjacent wire members. In the present embodiment, the densely wound portion of the second coil 22 is located at a distal portion and a proximal portion of the second coil 22, and the sparsely wound portion is located between the densely wound portion on a distal end side and the densely wound portion on a proximal end side. The second coil 22 may include only the densely wound portion without the sparsely wound portion.

A proximal portion of the first coil 21 and the distal portion of the second coil 22 are partially intertwined with each other. That is, the wire member of the proximal portion of the first coil 21 and the wire member of the distal portion of the second coil 22 are alternately arranged along the longitudinal direction. Accordingly, separation between the first coil 21 and the second coil 22 can be prevented. An intertwined length of the proximal portion of the first coil 21 and the distal portion of the second coil 22 can be, for example, 0.1 mm to 2 mm. The first coil 21 and the second coil 22 have the same winding direction such that the first coil 21 and the second coil 22 can be intertwined with each other.

Outer diameters of the wire members of the first coil 21 and the second coil 22 can be, for example, 20 μm to 90 μm, preferably 30 μm to 70 μm. In the present embodiment, the outer diameter of the wire member forming the first coil 21 is larger than the outer diameter of the wire member forming the second coil 22. Further, the wire members forming the first coil 21 and the second coil 22 may be not only one wire member, but also a twisted wire formed from two or more wire members.

The wire members of the first coil 21 and the second coil 22 are not particularly limited, and can be formed of a metal such as stainless steel, a super-elastic alloy, a cobalt-based alloy, gold, platinum, or tungsten, or an alloy containing these metals. For example, the first coil 21 can be made of a platinum-based alloy that is more flexible and has higher contrast than the second coil 22, and a material of the second coil 22 is made of a stainless steel. As the platinum-based alloy, Pt—Ir, Pt—Ni, Pt—W, or the like is preferably used.

The outer diameters of the first coil 21 and the second coil 22 are preferably constant from a distal end to a proximal end. In the present embodiment, the outer diameter of the first coil 21 is substantially equal to the outer diameter of the second coil 22. Accordingly, an outer diameter of the tubular body 20 is substantially constant from a distal end to a proximal end of the tubular body 20. The outer diameters of the first coil 21 and the second coil 22 can be, for example, 0.15 mm to 2 mm.

The material forming the wire members constituting the first coil 21 and the second coil 22, the outer diameters of the wire members, cross-sectional shapes of the wire members, pitches of the wire members, and the like can be appropriately selected according to the purpose of the guide wire 100. Further, the cross-sectional shape of the wire member is preferably a circular shape, but may be an elliptical shape or a polygonal shape. A center of a cross section of a wire member having a non-circular cross-sectional shape may be a centroid of the cross section of the wire member.

Fixing Portion

The fixing portion 30 is a member for fixing the tubular body 20 to the core component 10. In the present embodiment, the fixing portion 30 includes a distal end fixing portion 31 that fixes the distal end of the tubular body 20 to the core component 10, an intermediate fixing portion 32 that fixes an intermediate portion of the tubular body 20 to the core component 10, and a proximal end fixing portion 33 that fixes the proximal end of the tubular body 20 to the core component 10.

A material forming the fixing portion 30 can be, for example, a brazing material or a soldering material. Examples of the brazing material include gold brazing and silver brazing. Examples of the soldering material include Sn—Ag alloy soldering and Sn—Pb alloy soldering. The material forming the fixing portion 30 may be an adhesive.

The distal end fixing portion 31 fixes a distal portion of the first coil 21 to the flat portion 11*g* of the first core member 11. The distal end fixing portion 31 is located at a most distal end of the guide wire 100, and an outer surface of the distal end fixing portion 31 can be smoothly formed in a substantially hemispherical shape.

The intermediate fixing portion 32 fixes the proximal portion of the first coil 21 and the distal portion of the second coil 22 to the second tapered portion 11*e* of the first core member 11 via a cylindrical member 32*a*. The intermediate fixing portion 32 is provided at a position where the proximal portion of the first coil 21 and the distal portion of the second coil 22 are intertwined with each other in the first core member 11.

The cylindrical member 32*a* is disposed between an inner circumferential surface of the tubular body 20 and an outer circumferential surface of the core component 10. The cylindrical member 32*a* coaxially fixes the tubular body 20 and the core component 10 by reducing a gap between the inner circumferential surface of the tubular body 20 and the outer circumferential surface of the core component 10. In the present embodiment, an outer diameter of a distal portion of the cylindrical member 32*a* is smaller than an outer diameter of a proximal portion of the cylindrical member 32*a*. Accordingly, as illustrated in FIG. 2, the first coil 21 having a small inner diameter and the second coil 22 having a large inner diameter can be coaxially fixed to the core component 10. The outer diameter of the distal portion of the cylindrical member 32*a* and the outer diameter of the proximal portion of the cylindrical member 32*a* may be appropriately selected according to the inner diameter of the first coil 21 and the inner diameter of the second coil 22. The cylindrical member 32*a* can be formed of a metal or a resin material. The guide wire 100 may not include the cylindrical member 32*a*.

The proximal end fixing portion 33 fixes the proximal portion of the second coil 22 to the second constant outer diameter portion 11*d* of the first core member 11.

Cover Layer

The cover layer 40 includes a first cover layer 41, a second cover layer 42, and a third cover layer 43. The cover layer 40 can be formed of a material capable of reducing friction generated between the guide wire 100 and a blood vessel or a catheter. Accordingly, the cover layer 40 helps improve operability and safety of the guide wire 100.

The first cover layer 41 covers outer surfaces of the respective portions provided in the first core member 11 (the tubular body 20 and the fixing portion 30) and a portion of the first core member 11 (the second constant outer diameter portion 11*d*).

The second cover layer 42 covers a portion of the core component 10 located proximal of the tubular body 20. The second cover layer 42 covers an outer surface of a proximal portion of the first core member 11 (the first tapered portion 11*c* and the first constant outer diameter portion 11*b*) and the second core member 12. That is, the second cover layer 42 covers a portion of the core component 10 located proximal of the tubular body 20 except for the first bonding portion 11*a* and the second bonding portion 12*b*.

The third cover layer 43 covers outer surfaces of the first bonding portion 11*a* and the second bonding portion 12*b*.

The second cover layer 42 may cover an entire portion of the core component 10 located proximal of the tubular body 20. In this case, the third cover layer 43 is not provided. Alternatively, the second cover layer 42 may not cover a part of the portion of the core component 10 located proximal of the tubular body 20. In this case, the third cover layer 43 may be provided at a portion not covered with the second cover layer 42.

The first cover layer 41 can be formed of a hydrophilic polymer. Examples of the hydrophilic polymer forming the first cover layer 41 can include a cellulose-based polymer material, a polyethylene oxide-based polymer material, a maleic anhydride-based polymer material (for example, a maleic anhydride copolymer such as a methyl vinyl ether-maleic anhydride copolymer), an acrylamide-based polymer material (for example, polyacrylamide and a block copolymer of glycidyl methacrylate-dimethylacrylamide), a water-soluble nylon, polyvinyl alcohol, polyvinyl pyrrolidone, and derivatives of the hydrophilic polymers listed above.

The second cover layer 42 and the third cover layer 43 can be made of a low-friction material. Examples of the low friction material can include a polyolefin such as polyethylene and polypropylene, polyvinyl chloride, polyester (PET, PBT, or the like), polyamide, polyimide, polyurethane, polystyrene, polycarbonate, a silicone resin, a fluorine-based resin (PTFE, ETFE, or the like), and composite materials of the low-friction materials listed above.

The materials for forming the first cover layer 41, the second cover layer 42, and the third cover layer 43 are not limited to those described above. The first cover layer 41, the second cover layer 42, and the third cover layer 43 may be formed of different materials along the longitudinal direction of the core component 10. For example, in the second cover layer 42, a material covering a distal portion of the first core member 11 may be different from a material covering the proximal portion of the first core member 11. Further, the number of layers of each of the first cover layer 41, the second cover layer 42, and the third cover layer 43 may be plural (i.e., more than one). Any one of the first cover layer 41, the second cover layer 42, and the third cover layer 43 may not be provided.

The distal portion of the guide wire 100 according to the present embodiment has both the shaping property and the shape retaining property. The shaping property is a property that allows the operator to shape the distal portion of the guide wire 100. Since the guide wire 100 is given a desired shape to the distal portion by shaping, the operability of the guide wire 100 in a blood vessel and blood vessel selectivity at a branch portion can be improved. The shape given to the guide wire 100 by shaping depends on an inner diameter and a shape of a blood vessel of a patient. Therefore, it is preferable that the guide wire 100 can be rather easily shaped into the desired shape. That is, an excellent shaping property is required.

The shape retaining property is a property of maintaining, during an operation of the guide wire 100 in the blood vessel, the shape given to the distal portion of the guide wire 100 by the operator by shaping. In general, the shape given to the guide wire 100 by shaping is a curved shape, and a curvature radius of the curved shape is larger than the inner diameter of the blood vessel. Therefore, the guide wire 100 is deformed in accordance with the inner diameter and the shape of the blood vessel. Further, the guide wire 100 may be unintentionally bent into a U-shape when the distal portion of the guide wire 100 comes into contact with a blood vessel wall of the branch portion or is caught on the stent. Furthermore, the guide wire 100 may be intentionally bent into a U-shape for a purpose of preventing blood vessel perforation when passing through the stenosis. As described above, the distal portion of the guide wire 100 receives an external force that can deform the distal portion during the operation in the blood vessel. When restorability of the guide wire 100 against the external force is relatively low, the guide wire 100 is plastically deformed and cannot maintain the shape given by the operator by shaping, and the operability and the blood vessel selectivity decrease. When the distal portion of the guide wire is deformed, the operator needs to remove the guide wire from the blood vessel and reshape the guide wire. When the guide wire is deformed to such an extent of being difficult to reshape, it is necessary to replace the guide wire with another guide wire. Accordingly, procedure time can be extended, and burden on the operator and the patient can be increased. Therefore, it is preferable that the guide wire 100 has a restorability such that even the guide wire 100 can be deformed by receiving the external force during the operation in the blood vessel, the guide wire 100 can be restored to the shape given by the operator by shaping when the external force is removed. That is, the guide wire 100 is required to have an excellent shape retaining property.

The guide wire 100 having both the shaping property and the shape retaining property can be obtained by controlling an elastic portion of total indentation work and Martens hardness of the distal portion of the guide wire 100 formed of a Ni—Ti alloy to be within predetermined ranges.

The elastic portion of total indentation work and the Martens hardness are calculated from a load-displacement curve obtained by an instrumented indentation hardness test for the flat portion 11*g* of the guide wire 100. The elastic portion of total indentation work is a ratio of a work of elastic deformation to a total work (a sum of a work of plastic deformation and the work of elastic deformation). The Martens hardness is a value obtained by dividing a test load by a surface area of indentation by an indenter in the instrumented indentation hardness test.

A material having a large elastic portion of total indentation work has a relatively high restorability of a shape caused by superelasticity. Therefore, even an external force is applied to the flat portion 11*g* of the guide wire 100 formed of a material having a large elastic portion of total indentation work, the flat portion 11*g* is rather easily restored to an original shape when the external force is removed. Accordingly, the larger the elastic portion of total indentation work, the lower the shaping property of the flat portion 11*g*, and the higher the shape retaining property. On the other hand, a material having a small elastic portion of total indentation work is likely to be plastically deformed. Therefore, a flat portion 11*g* formed of a material having a small elastic portion of total indentation work is plastically deformed when the external force is applied, and the shape of the flat portion 11*g* can be rather easily maintained even when the external force is removed. Accordingly, the smaller the elastic portion of total indentation work, the higher the shaping property and the lower the shape retaining property of the flat portion 11*g*.

A material having a high Martens hardness is relatively hard. Therefore, a flat portion 11*g* of the guide wire 100 formed of a material having a high Martens hardness is unlikely to be deformed by an external force. Accordingly, the higher the Martens hardness, the lower the shaping property of flat portion 11*g* and the higher the shape retaining property. On the other hand, a flat portion 11*g* of the guide wire 100 formed of a material having a low Martens hardness is likely to be plastically deformed even by a small external force received in the blood vessel. Accordingly, the smaller the Martens hardness, the higher the shaping property and the lower the shape retaining property of the flat portion 11*g*.

A magnitude of the external force received by the guide wire 100 in the blood vessel is smaller than that of the external force applied by the operator for shaping. Therefore, the distal portion of the guide wire 100 can have both the shaping property and the shape retaining property by having a physical property capable of being deformed by a relatively large force applied by the operator for shaping, and capable of restoring the shape at the time of shaping without being plastically deformed by a small force applied during a procedure.

The Martens hardness can have a greater influence on the shaping property and the shape retaining property than the elastic portion of total indentation work. Accordingly, the shaping property and the shape retaining property cannot be both improved when only the elastic portion of total indentation work is controlled, and it is particularly necessary to appropriately control the Martens hardness.

The flat portion 11*g* of the guide wire 100 according to the present embodiment can be formed of a Ni—Ti alloy having, for example, an elastic portion of total indentation work of 46.0% to 59.5% and having a Martens hardness of 1300 N/mm$^2$ to 3000 N/mm$^2$.

The distal portion of the guide wire 100 in which the flat portion 11*g* has the elastic portion of total indentation work and the Martens hardness in the above ranges has the physical property capable of being deformed by the large force applied by the operator for shaping, and capable of restoring the shape at the time of shaping without being plastically deformed by the small force applied during the procedure. Accordingly, the guide wire 100 can be shaped by the operator, and can be restored to the shape at the time of shaping even an external force that can deform the distal portion is received in a blood vessel. Therefore, the guide wire can maintain relatively high operability and blood vessel selectivity given by shaping even during the procedure. Further, the operator does not need to remove the guide wire 100 from the blood vessel and reshape the guide wire 100 or replace the guide wire 100 with another guide wire, and thus the procedure can be rather easily performed. Accordingly, the procedure time can be shortened, and thus the burden on the operator and the patient can be reduced.

Further, the flat portion 11*g* of the guide wire 100 preferably, for example, has an elastic portion of total indentation work of 46.0% to 59.5% and has a Martens hardness of 1300 N/mm$^2$ to 2120 N/mm$^2$. By setting the elastic portion of total indentation work of the flat portion 11*g* of the guide wire 100 in the range of 46.0% to 59.5% and the Martens hardness in the range of 1300 N/mm$^2$ to 2120 N/mm$^2$, the flat portion 11*g* of the first core member 11 is more flexible, and thus the shaping property can be further improved.

Further, in the guide wire 100, the distal portion of the core component 10 is preferably subjected to heat treatment in order to set the elastic portion of total indentation work and the Martens hardness of the flat portion 11*g* in the above ranges.

The flat portion 11*g* is formed by pressing the distal portion of the first core member 11 made of a Ni—Ti alloy. The flat portion 11*g* after pressing has lower superelasticity than the Ni—Ti alloy before pressing due to a strain introduced by the pressing. Therefore, the flat portion 11*g* after press has a small elastic portion of total indentation work, and thus has a low shape retaining property. By subjecting the flat portion 11*g* after pressing to heat treatment, the strain can be removed from the flat portion 11*g*, and the superelasticity can be improved. As a result, the flat portion 11*g* has a large elastic portion of total indentation work and has an improved shape retaining property. Further, the flat portion 11*g* after pressing is harder than the Ni—Ti alloy before pressing by work hardening. Therefore, the flat portion 11*g* after pressing has a high Martens hardness and thus has a low shaping property. By subjecting the flat portion 11*g* after pressing to heat treatment, the flat portion 11*g* is softer. As a result, flat portion 11*g* has a low Martens hardness, and has an improved shaping property. In this way, in the guide wire 100, the elastic portion of total indentation work and the Martens hardness of the distal portion of the guide wire 100 formed of a Ni—Ti alloy can be controlled within predetermined ranges by subjecting the pressed flat portion 11*g* to heat treatment. Accordingly, the guide wire 100 can have both the shaping property and the shape retaining property.

Heat treatment is preferably performed in a region of the flat portion 11*g* and at least a part of the transition portion 11*f* of the first core member 11. That is, the guide wire 100 according to the present embodiment has a heat treatment region H continuously extending from the distal end of the flat portion 11*g* to the at least a part of the transition portion 11*f* along the longitudinal direction. One end of the heat treatment region H of the guide wire 100 coincides with the distal end of the flat portion 11*g*, and the other end is located at the transition portion 11*f*. In the present specification, the heat treatment region H refers to a region where an oxide film is formed on at least a part of the outer surface of the first core member in the circumferential direction by heat treatment. Therefore, in the guide wire 100, an oxide film is formed on an outer surface from the distal end of the flat portion 11*g* to the at least a part of the transition portion 11*f* along the longitudinal direction. Further, in the present specification, a total length from one end to the other end of the heat treatment region H of the guide wire 100 along the longitudinal direction is referred to as a heat treatment length. The heat treatment length of the guide wire 100 is longer than the length of the flat portion 11*g* along the longitudinal direction.

Figure 4A:
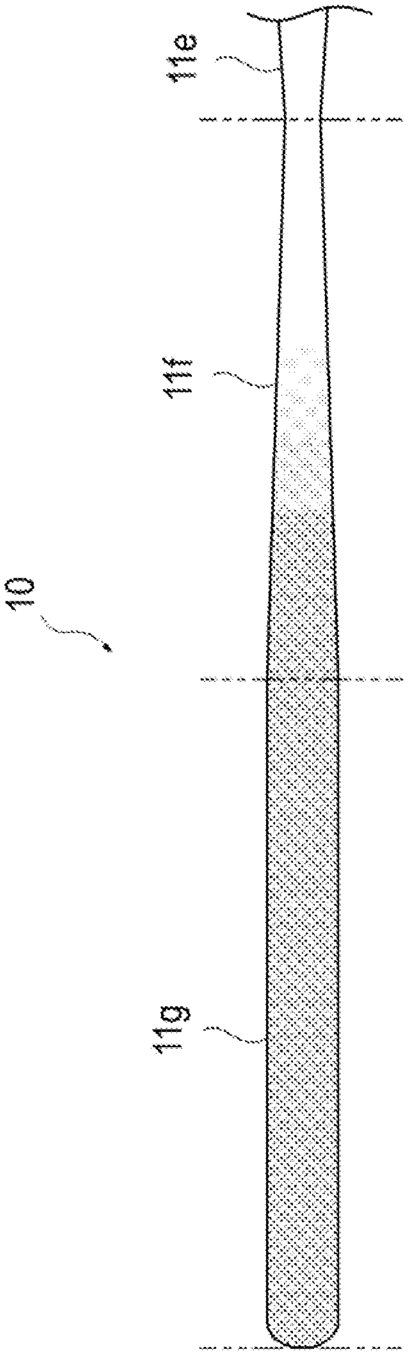
FIG. 4A is a conceptual diagram illustrating a state of rigidity of the first core member of the guide wire according to the present embodiment before heat treatment.
Figure 4B:
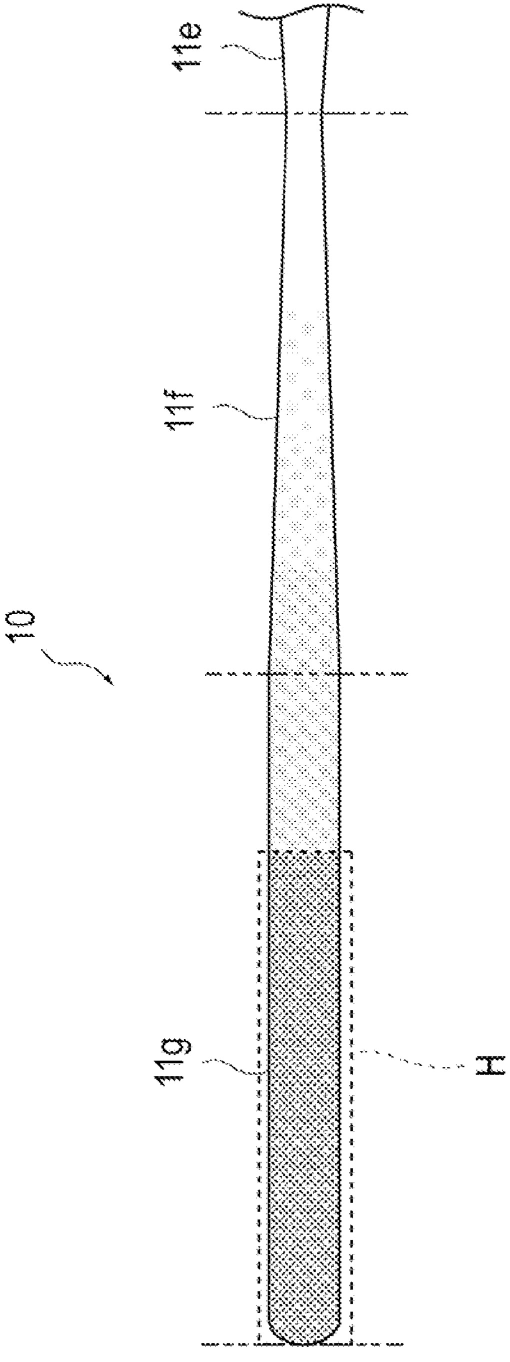
FIG. 4B is a conceptual diagram schematically illustrating the rigidity when only a portion of a flat portion is subjected to heat treatment in the first core member of the guide wire according to the present embodiment.
Figure 4C:
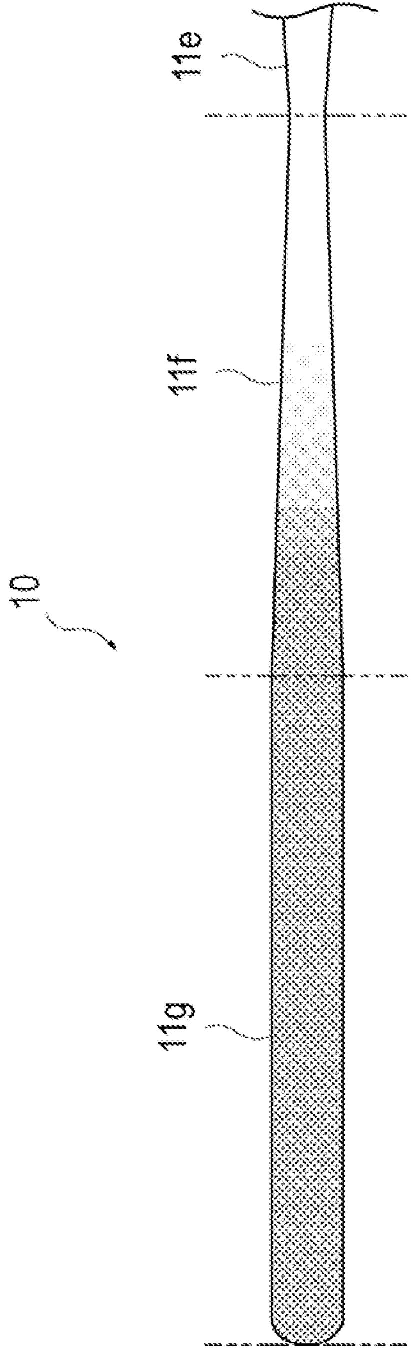
FIG. 4C is a conceptual diagram schematically illustrating a state of the rigidity when heat treatment is applied to a part of transition portion in addition to the flat portion in the first core member of the guide wire according to the present embodiment.

Since the guide wire 100 includes the heat treatment region H continuously extending from the distal end of the flat portion 11*g* to the at least a part of the transition portion 11*f*, it is possible to prevent a sudden change in rigidity of the guide wire 100 along the longitudinal direction. FIGS. 4A-4C are diagrams schematically illustrating the rigidity of the distal portion of the first core member 11 when the guide wire 100 is subjected to heat treatment. In FIGS. 4A and 4C, dot groups appearing on an outer surface of the first core member 11 express a level of rigidity, with denser dots indicating lower rigidity and sparser dots indicating higher rigidity. Two-dot chain lines in FIGS. 4A-4C are imaginary lines that partition regions of the flat portion 11*g*, the transition portion 11*f*, and the second tapered portion 11*e*. As illustrated in FIG. 4A, in the guide wire 100, the flat portion 11*g* has a flat shape with a relatively small thickness. Therefore, rigidity of the flat portion 11*g* is relatively low and is constant along the longitudinal direction. On the other hand, the transition portion 11*f* has the wedge shape in which the thickness gradually increases and the width gradually decreases from the flat portion 11*g* toward the second tapered portion 11*e*. Therefore, rigidity of the transition portion 11*f* is equal to that of the flat portion 11*g* at the distal end, and gradually increases from the distal end toward the proximal end. Here, when the first core member 11 is subjected to heat treatment, the rigidity of the portion of the first core member 11 subjected to heat treatment decreases. Accordingly, as illustrated in FIG. 4B, when only a part of the flat portion 11*g* is subjected to heat treatment, the rigidity of the flat portion 11*g* suddenly changes at a position of a proximal end of the heat treatment region H. Alternatively, when only the flat portion 11*g* is subjected to heat treatment, the rigidity of the first core member 11 suddenly changes at a boundary between the flat portion 11*g* and the transition portion 11*f*. The guide wire 100 is likely to be bent at a point where the rigidity suddenly changes along the longitudinal direction, and is likely to cause prolapse. In the present embodiment, as illustrated in FIG. 4C, it is preferable that the flat portion 11*g* is subjected to heat treatment over an entire length of the flat portion 11*g*, and in addition, a part of the transition portion 11*f* is also subjected to heat treatment. As a result, in the guide wire 100, the sudden change in rigidity along the longitudinal direction can be prevented, and prolapse resistance can be improved.

The "prolapse" means a state in which, when the distal end of the guide wire 100 is inserted into a side branch from a main duct, a portion of the guide wire 100 proximal of the distal end is locally bent, and the bent portion deviates distal of a branch from the main duct to the side branch. When the guide wire 100 is in such a state, since a pushing force or torque applied to the proximal end of the guide wire 100 is transmitted only to the bent portion, it can be difficult for the operator to advance the distal end of the guide wire 100 to a distal end of the side branch. Further, since a distal end of the catheter advanced along the guide wire 100 is guided to the bent portion, it can be difficult for the operator to advance the catheter to the side branch.

The proximal end of the heat treatment region H of the guide wire 100 is preferably located at the transition portion 11*f*. That is, the proximal end of the heat treatment region H of the guide wire 100 is preferably not located at the second tapered portion 11*e*. When the second tapered portion 11*e* not subjected to cold working is subjected to heat treatment, the superelasticity decreases, and plastic deformation is likely to occur. As a result, the guide wire 100 is likely to be kinked in the blood vessel. In the present embodiment, as illustrated in FIG. 4C, only the flat portion 11*g* and the transition portion 11*f* subjected to cold working are subjected to heat treatment. Accordingly, plastic deformation of the guide wire 100 due to the decrease in the superelasticity can be prevented, and the kink resistance can be improved.

In the guide wire 100, a ratio of a length from the distal end of the transition portion 11*f* to the proximal end of the heat treatment region H along the longitudinal direction to the length of the transition portion 11*f* along the longitudinal direction can be, for example, preferably 10% to 100%. Accordingly, the guide wire 100 can improve the prolapse resistance and the kink resistance while having the shaping property and the shape retaining property. When the heat treatment length is longer than the above range, a portion of the first core member 11 not subjected to cold working, such as the second tapered portion 11*e*, is subjected to heat treatment. When the portion of the first core member 11 not subjected to cold working is subjected to heat treatment, the superelasticity decreases, and plastic deformation is likely to occur. As a result, the guide wire 100 is likely to be kinked in the blood vessel. Further, when the heat treatment length is shorter than the above range and only the flat portion 11*g* is subjected to heat treatment, the rigidity of the first core member 11 is suddenly changed at the rigidity in the boundary between the flat portion 11*g* and the transition portion 11*f* and prolapse is likely to occur.

In the guide wire 100, the ratio of the length from the distal end of the transition portion 11*f* to the proximal end of the heat treatment region H along the longitudinal direction to the length of the transition portion 11*f* along the longitudinal direction can be, for example, more preferably 55% to 65%. Accordingly, the guide wire 100 can further improve the prolapse resistance and the kink resistance while having the shaping property and the shape retaining property. When the length from the distal end of the transition portion 11*f* to the proximal end of the heat treatment region H along the longitudinal direction exceeds 65% of the length of the transition portion 11*f* along the longitudinal direction, a length of the portion of the transition portion 11*f* having decreased rigidity due to heat treatment is longer. Therefore, when the guide wire 100 is pushed in a state in which the distal end of the guide wire 100 is inserted into a side branch from a main duct, the pushing force is not transmitted to the distal end of the guide wire 100, and the guide wire 100 is bent at the transition portion 11*f* located in the main duct, and prolapse is likely to occur. On the other hand, when the length from the distal end of the transition portion 11*f* to the proximal end of the heat treatment region H along the longitudinal direction is less than 55% of the length of the transition portion 11*f* along the longitudinal direction, a length of the portion of the transition portion 11*f* having a relatively high rigidity is longer. Further, since the proximal end of the heat treatment region H is disposed at the distal portion of the transition portion 11*f* having a relatively low rigidity, the rigidity of the guide wire 100 suddenly changes at the proximal end of the heat treatment region H, and prolapse is likely to occur. By setting the length of the heat treatment region H from the distal end of the transition portion 11*f* to the proximal end of the heat treatment region H along the longitudinal direction to 55% to 65% of the length of the transition portion 11*f* along the longitudinal direction, the guide wire 100 can further improve the prolapse resistance and the kink resistance.

Various conditions for performing heat treatment on the distal portion of the core component 10 can be appropriately set. For example, a temperature at which heat treatment is performed can be 300° C. to 650° C., and time can be 3 minutes to 60 minutes.

Heat treatment has an effect of softening the flat portion 11*g* hardened by cold working and making the flat portion 11*g* relatively easier to deform, and an effect of removing the strain from the flat portion 11*g* having decreased superelasticity due to the strain introduced by cold working to appropriately improve the superelasticity. Accordingly, heat treatment is particularly effective as a method of giving the shaping property and the shape retaining property to the guide wire 100. The method of giving the shaping property and the shape retaining property to the distal portion of the core component 10 is not limited to heat treatment, and other methods may be applied as long as the elastic portion of total indentation work and the Martens hardness can be in the above ranges.

Operations and Effects

As described above, the guide wire 100 according to the present embodiment includes the elongated core component 10 having the flat portion 11*g* at the distal end. The flat portion 11*g* is made of a Ni—Ti alloy having an elastic portion of total indentation work, for example, of 46.0% to 59.5% and having a Martens hardness of 1300 $N/mm^2$ to 3000 $N/mm^2$.

With such a configuration, the guide wire 100 can have the physical property capable of being deformed by a large force applied by an operator for shaping, and capable of restoring the shape at the time of shaping without being plastically deformed by a small force applied during the procedure. That is, the guide wire 100 can have both the shaping property and the shape retaining property. Accordingly, the guide wire 100 can be shaped by the operator, and can be restored to the shape at the time of shaping even an external force that can deform the distal portion is received in a blood vessel. Therefore, the guide wire 100 can maintain the relatively high operability and blood vessel selectivity given by shaping even during a procedure. Further, the operator does not need to remove the guide wire 100 from the blood vessel and reshape the guide wire 100 or replace the guide wire 100 with another guide wire, and thus the procedure can be rather easily performed. Accordingly, the procedure time can be shortened, and thus the burden on the operator and the patient can be reduced.

Further, the guide wire 100 according to the present embodiment may have a Martens hardness, for example, of 1300 $N/mm^2$ to 2120 $N/mm^2$.

With such a configuration, in the guide wire 100, the flat portion 11*g* of the first core member 11 located at the distal end of the core component 10 is more flexible, and thus shaping property can be further improved.

Further, the core component 10 of the guide wire 100 according to the present embodiment may include, in order from the distal end side, the flat portion 11*g* and the transition portion 11*f* extending from the proximal end of the flat portion 11*g* toward the proximal end side along the longitudinal direction, and the core component 10 may include the heat treatment region H extending from the distal end of the flat portion 11*g* to at least a part of the transition portion 11*f*.

With such a configuration, since the first core member 11 can help prevent a sudden change in the rigidity along the longitudinal direction at the proximal end of the heat treatment region H, the prolapse resistance and the kink resistance can be improved while having the shaping property and the shape retaining property.

Further, in the guide wire 100 according to the present embodiment, the ratio of the length from the distal end of the transition portion 11*f* to the proximal end of the heat treatment region H along the longitudinal direction to the length of the transition portion 11*f* along the longitudinal direction may be, for example, 10% to 100%.

With such a configuration, the guide wire 100 can help improve the prolapse resistance and the kink resistance while having the shaping property and the shape retaining property.

Further, in the guide wire 100 according to the present embodiment, the ratio of the length from the distal end of the transition portion 11*f* to the proximal end of the heat treatment region H along the longitudinal direction to the length of the transition portion 11*f* along the longitudinal direction may be, for example, 55% to 65%.

With such a configuration, since the guide wire 100 can further prevent a sudden change in the rigidity of the guide wire 100 along the longitudinal direction, the prolapse resistance and the kink resistance can be further improved.

Further, a method of manufacturing the guide wire 100 including the core component 10 according to the present embodiment includes: performing cold working on the distal portion of the core component 10 such that the distal portion includes the flat portion 11*g* and the transition portion 11*f* extending from the proximal end of the flat portion 11*g* toward the proximal end side along the longitudinal direction; and performing heat treatment on the flat portion 11*g* and at least a part of the transition portion 11*f* such that the elastic portion of total indentation work of the flat portion 11*g* is, for example, 46.0% to 59.5% and the Martens hardness of the flat portion 11*g* is, for example, 1300 $N/mm^2$ to 3000 $N/mm^2$.

The guide wire 100 manufactured by the above method can have the physical property capable of being deformed by the large force applied by the operator for shaping, and capable of restoring the shape at the time of shaping without being plastically deformed by the small force applied during the procedure. That is, the guide wire 100 can have both the shaping property and the shape retaining property. Accordingly, the guide wire 100 can be shaped by the operator, and can be restored to the shape at the time of shaping even an external force that can deform the distal portion is received in a blood vessel. Therefore, the guide wire 100 can maintain the high operability and blood vessel selectivity given by shaping even during the procedure. Further, the operator does not need to remove the guide wire 100 from the blood vessel and reshape the guide wire 100 or replace the guide wire 100 with another guide wire, and thus the procedure can be rather easily performed. Accordingly, the procedure time is shortened, and thus the burden on the operator and the patient can be reduced. Further, heat treatment has an effect of softening the flat portion 11*g* hardened by cold working and making the flat portion 11*g* easier to deform, and an effect of removing the strain from the flat portion 11*g* having decreased superelasticity due to the strain introduced by cold working to appropriately improve the superelasticity. Therefore, heat treatment can be particularly effective as a method of giving the shaping property and the shape retaining property to the guide wire 100.

EXAMPLES

Hereinafter, the disclosure will be described in detail with reference to examples, but the scope of the disclosure is not limited to the following examples.

Hereinafter, "manufacture of guide wire", "evaluation method", and "evaluation result" of the guide wires 100 in the examples and comparative examples will be described in detail with reference to Table 1 to Table 4 (FIGS. 8-11). Table 1 (FIG. 8) illustrates manufacture conditions in Example 1 to Example 16, and Table 2 (FIG. 9) illustrates manufacture conditions in Comparative Example 1 to Comparative Example 4. A "heat treatment ratio" in each of Table 1 (FIG. 8) and Table 2 (FIG. 9) is the ratio of the length from the distal end of the transition portion 11*f* to the proximal end of the heat treatment region H along the longitudinal direction to the length of the transition portion 11*f* along the longitudinal direction.

Manufacture of Guide Wire

Hereinafter, the manufacture of the guide wire 100 according to the examples and the comparative examples will be described. In each of the examples and the comparative examples, heat treatment performed in step 3 was performed at a temperature in the range of 300° C. to 650° C. and for a time in the range of 3 minutes to 60 minutes.

Example 1

Step 1

The distal portion of the first core member 11 made of a Ni—Ti alloy (Ni content: 54 mass % to 57 mass %) was tapered such that the outer diameter of the first core member 11 gradually decreased from the proximal end side toward the distal end side. The outer diameter of the most distal portion was 80 μm.

Step 2

A range of 16 mm from the distal end toward the proximal end side of the first core member 11 was pressed to form the flat portion 11*g* and the transition portion 11*f*. At this time, a range of 9 mm from the distal end toward the proximal end side of the guide wire 100 was defined as the flat portion 11*g*, and was formed into a flat shape having a constant thickness of 27 μm. A range of 7 mm from the proximal end of the flat portion 11*g* toward the proximal end side of the guide wire 100 was defined as the transition portion 11*f*, and was processed into a wedge shape in which the thickness increased toward the proximal end side.

Step 3

Heat treatment was performed in a range of 12.5 mm from the most distal end toward the proximal end side of the first core member 11 pressed in step 2.

Step 4

The tubular body 20 including the first coil 21 and the second coil 22 is disposed around from the flat portion 11*g* of the first core member 11 to a part of the second constant outer diameter portion 11*d*. As the first coil 21, a coil having a length of 28 mm to 32 mm formed by winding a wire member (outer diameter: 0.340 mm to 0.350 mm, wire member diameter: 58 μm to 60 μm) made of a platinum-based alloy was used. As the second coil 22, a coil having a length of 210 mm to 220 mm formed by winding a wire member (outer diameter: 0.340 mm to 0.350 mm, wire member diameter: 38 μm to 40 μm) made of a stainless steel was used. The distal portion of the first coil 21 was fixed to the flat portion 11*g* of the first core member 11 with silver brazing. The proximal portion of the first coil 21 and the distal portion of the second coil 22 were fixed to the second tapered portion 11*e* of the first core member 11 by a Sn—Ag alloy solder via the metallic cylindrical member 32*a*. The proximal portion of the second coil 22 was fixed to the second constant outer diameter portion 11*d* of the first core member 11 by a Sn—Ag alloy solder.

Step 5

The first core member 11 and the second core member 12 were bonded by resistance butt welding.

Step 6

Outer surfaces of the first coil 21, the second coil 22, and a part of the second constant outer diameter portion 11*d* were coated with a hydrophilic polymer to form the first cover layer 41. Outer surfaces of the first constant outer diameter portion 11*b*, the first tapered portion 11*c* of the first core member 11 and the second core member 12 were coated with a fluorine-based resin to form the second cover layer 42. Outer surfaces of the first bonding portion 11*a* and the second bonding portion 12*b* were coated with a silicone resin to form the third cover layer 43.

The guide wires in Examples 2 to 16 were manufactured as follows. The guide wires in Examples 2 to 6 and 9 to 16 were manufactured in the same manner as in Example 1 in step 1, step 2, and step 4 to step 6, and were manufactured in step 3 as follows.

Example 2

In step 3, heat treatment was performed in a range of 13.0 mm from the most distal end toward the proximal end side of the first core member 11 pressed in step 2.

Example 3

In step 3, heat treatment was performed in a range of 13.8 mm from the most distal end toward the proximal end side of the first core member 11 pressed in step 2.

Example 4

In step 3, heat treatment was performed in a range of 13.6 mm from the most distal end toward the proximal end side of the first core member 11 pressed in step 2.

Example 5

In step 3, heat treatment was performed in a range of 12.8 mm from the most distal end toward the proximal end side of the first core member 11 pressed in step 2.

Example 6

In step 3, heat treatment was performed in a range of 13.3 mm from the most distal end toward the proximal end side of the first core member 11 pressed in step 2.

Example 9

In step 3, heat treatment was performed in a range of 7.2 mm from the most distal end toward the proximal end side of the first core member 11 pressed in step 2.

Example 10

In step 3, heat treatment was performed in a range of 9.3 mm from the most distal end toward the proximal end side of the first core member 11 pressed in step 2.

Example 11

In step 3, heat treatment was performed in a range of 10.3 mm from the most distal end toward the proximal end side of the first core member 11 pressed in step 2.

Example 12

In step 3, heat treatment was performed in a range of 11.7 mm from the most distal end toward the proximal end side of the first core member 11 pressed in step 2.

Example 13

In step 3, heat treatment was performed in a range of 14.4 mm from the most distal end toward the proximal end side of the first core member 11 pressed in step 2.

Example 14

In step 3, heat treatment was performed in a range of 16.0 mm from the most distal end toward the proximal end side of the first core member 11 pressed in step 2.

Example 15

In step 3, heat treatment was performed in a range of 18.9 mm from the most distal end toward the proximal end side of the first core member 11 pressed in step 2.

Example 16

In step 3, heat treatment was performed in a range of 20.6 mm from the most distal end toward the proximal end side of the first core member 11 pressed in step 2.

Further, the guide wires in Example 7 and Example 8 were manufactured in the same manner as in Example 1 in step 1 and step 4 to step 6, and were manufactured in step 2 and step 3 as follows.

Example 7

Step 2

The range of 16 mm from the distal end toward the proximal end side of the first core member 11 was pressed to form the flat portion 11*g* and the transition portion 11*f*. At this time, a range of 13 mm from the distal end toward the proximal end side of the guide wire 100 was defined as the flat portion 11*g*, and was formed into a flat shape having a constant thickness of 32 μm. A range of 3 mm from the proximal end of the flat portion 11*g* toward the proximal end side of the guide wire 100 was defined as the transition portion 11*f*, and was processed into a wedge shape in which the thickness increased toward the proximal end side.

Step 3

Heat treatment was performed in a range of 13.6 mm from the most distal end toward the proximal end side of the first core member 11 pressed in step 2.

Example 8

Step 2

The range of 16 mm from the distal end toward the proximal end side of the first core member 11 was pressed to form the flat portion 11*g* and the transition portion 11*f*. At this time, a range of 13 mm from the distal end toward the proximal end side of the guide wire 100 was defined as the flat portion 11*g*, and was formed into a flat shape having a constant thickness of 32 μm. A range of 3 mm from the proximal end of the flat portion 11*g* toward the proximal end side of the guide wire 100 was defined as the transition portion 11*f*, and was processed into a wedge shape in which the thickness increased toward the proximal end side.

Step 3

Heat treatment was performed in a range of 13.7 mm from the most distal end toward the proximal end side of the first core member 11 pressed in step 2.

The guide wires in Comparative Examples 1 to 4 were manufactured as follows. The guide wires in Comparative Example 1 and Comparative Example 2 were manufactured in the same manner as in Example 1 in step 1, step 2, and step 4 to step 6, and were manufactured in step 3 as follows.

Comparative Example 1

In step 3, the first core member 11 pressed in step 2 was not subjected to the heat treatment.

Comparative Example 2

In step 3, heat treatment was performed in a range of 13.7 mm from the most distal end toward the proximal end side of the first core member 11 pressed in step 2.

Further, the guide wires in Comparative Example 3 and Comparative Example 4 were manufactured as follows. The guide wires in Comparative Example 3 and Comparative Example 4 were manufactured in the same manner as in Example 1 in step 1 and step 4 to step 6, and were manufactured in step 2 and step 3 as follows.

Comparative Example 3

Step 2

The range of 16 mm from the distal end toward the proximal end side of the first core member 11 was pressed to form the flat portion 11*g* and the transition portion 11*f*. At this time, a range of 13 mm from the distal end toward the proximal end side of the guide wire 100 was defined as the flat portion 11*g*, and was formed into a flat shape having a constant thickness of 32 μm. A range of 3 mm from the proximal end of the flat portion 11*g* toward the proximal end side of the guide wire 100 was defined as the transition portion 11*f*, and was processed into a wedge shape in which the thickness increased toward the proximal end side.

Step 3

Heat treatment was performed in a range of 14.3 mm from the most distal end toward the proximal end side of the first core member 11 pressed in step 2.

Comparative Example 4

Step 2

The range of 16 mm from the distal end toward the proximal end side of the first core member 11 was pressed to form the flat portion 11*g* and the transition portion 11*f*. At this time, a range of 13 mm from the distal end toward the proximal end side of the guide wire 100 was defined as the flat portion 11*g*, and was formed into a flat shape having a constant thickness of 32 μm. A range of 3 mm from the proximal end of the flat portion 11*g* toward the proximal end side of the guide wire 100 was defined as the transition portion 11*f*, and was processed into a wedge shape in which the thickness increased toward the proximal end side.

Step 3

Heat treatment was performed in a range of 13.0 mm from the most distal end toward the proximal end side of the first core member 11 pressed in step 2.

Evaluation Method

Evaluation of the guide wires 100 in Example 1 to Example 16 and Comparative Example 1 to Comparative Example 4 was performed as follows.

Measurement of Elastic Portion of Total Indentation Work and Martens Hardness

Device

Dynamic Ultra Micro Rigidity Tester DUH-211S manufactured by Shimadzu Corporation Measurement Conditions Measurement indenter: triangular pyramid indenter (dihedral angle) 115° equipment accessory (Triangular 115)

Environmental conditions: temperature 22±1° C.

Measurement Method and Procedure

Test method: load-unload test (complied to "Instrumented indentation test for hardness" ISO 14577-1)

Indentation depth: 0.5 μm

Holding time: 0 seconds

Measurement position: any 10 locations on a cross section parallel to a plane viewed from the thickness direction of the flat portion 11*g*.

Calculation Method

The elastic portion of total indentation work and the Martens hardness of the guide wire 100 in each of the examples and the comparative examples were average values of measured values at any 10 locations on the cross section parallel to the plane viewed from the thickness direction of the flat portion 11*g*. The elastic portion of total indentation work was rounded to one decimal place, and the Martens hardness was rounded to an integer.

Shaping Property Test

A shaping test was performed as follows. First, a portion of 5 mm from the distal end of the guide wire 100 was sandwiched between a silicone rubber plate placed on a substantially horizontal surface and a round rod (+0.7 mm) made of stainless steel, and the round rod was pressed with a load of 100 g. Next, the guide wire 100 was pulled out from the silicone rubber plate in a vertical direction, and the shape of the distal portion of the guide wire 100 was visually observed. In a case in which the distal portion of the guide wire 100 after the test was significantly deformed as compared with that before the test, the evaluation was "good", in a case in which the distal portion was deformed but by a small degree, the evaluation was "fair", and in a case in which the distal portion was not deformed, the evaluation was "poor".

Shape Retaining Property Test

A shape retaining property test was performed as follows. The guide wire 100 was deformed and shaped at a radius of curvature of 3.5 mm from a position of 2 mm to a position of 7 mm from the distal end of the guide wire 100. The shaped guide wire 100 was inserted into a U-shaped passage having a radius of curvature of 15 mm, and the guide wire 100 was pulled out after being alternately rotated 10 times in total on left and right sides, and the shape of the distal portion of the guide wire 100 was confirmed. When a perpendicular line was drawn from the distal end of the guide wire 100 to the central axis C, in a case in which a distance between a foot of the perpendicular line before the test and a foot of the perpendicular line after the test on the central axis C was 1 mm or less, the shape was considered to be retained and the evaluation was "good", and in a case in which the distance was larger than 1 mm, the shape was considered to be unable to be retained, and the evaluation was "poor". The smaller the radius of curvature of the U-shaped passage, the greater the external force applied to the guide wire 100, which makes it difficult to maintain the shape of the guide wire 100 during shaping.

Prolapse Resistance Test

Figure 5A:
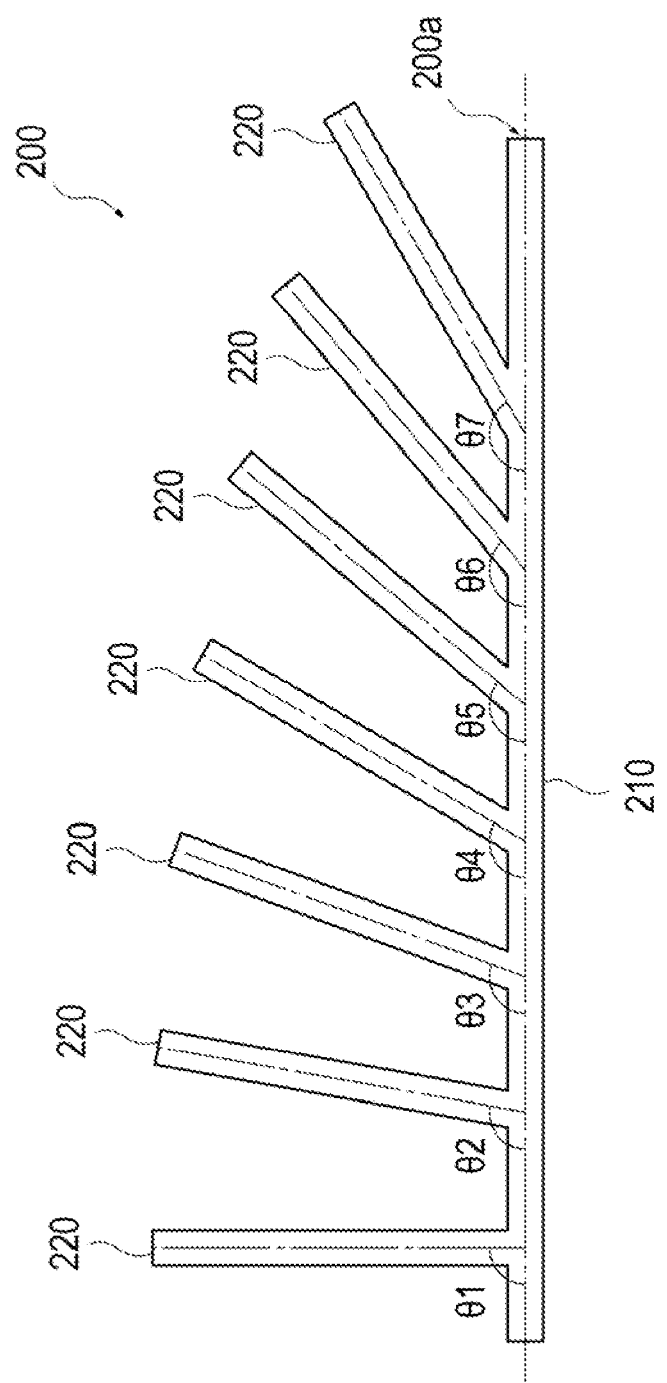
FIG. 5A is a schematic configuration diagram of a branch model used in a prolapse resistance test.

A prolapse resistance test was performed as follows. First, a branch model 200 made of a silicone resin tube illustrated in FIG. 5A was prepared. The branch model 200 includes a main duct 210 and a plurality of side branches 220 disposed along a longitudinal direction of the main duct 210. The main duct 210 has an inner diameter of 3 mm, and the side branch 220 has an inner diameter of 2 mm. In FIG. 5A, angles θ (θ1 to θ7) between a central axis of the main duct 210 and central axes of the side branches 220 on the distal end side were θ1=90°, θ2=100°, θ3=110°, θ4=120°, θ5=130°, θ6=140°, and θ7=150°.

Figure 5B:
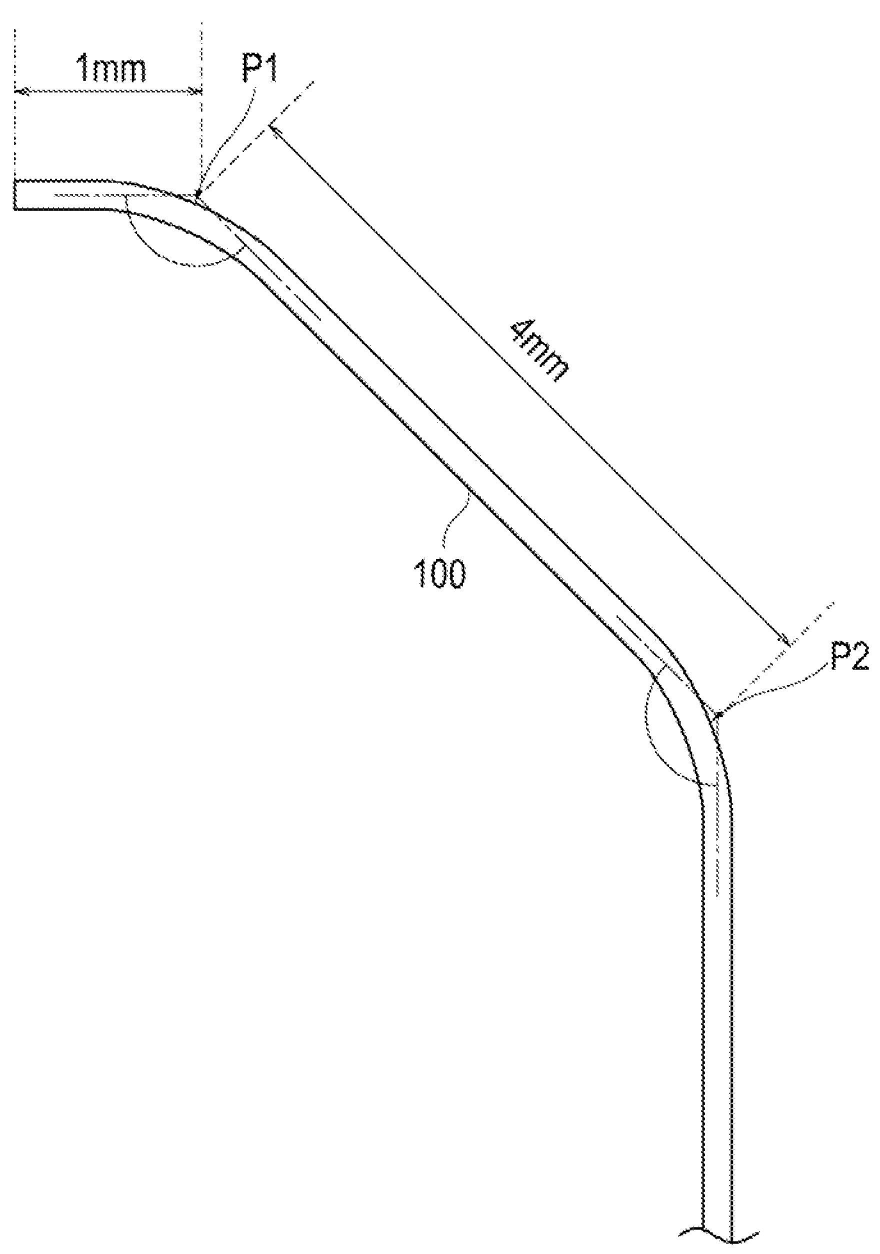
FIG. 5B is a diagram illustrating a shaped shape of the distal portion of the guide wire.

Next, the distal portion of the guide wire 100 was shaped. As illustrated in FIG. 5B, the shaping was performed by deforming the guide wire 100 in the same direction by approximately 135° at each of a first bending point P1 at a position 1 mm from the distal end of the guide wire 100 and a second bending point P2 at a position 5 mm from the distal end. Next, the guide wire 100 was inserted into each side branch 220 from an insertion opening 200*a* of the branch model 200 filled with water. Among the side branches 220 into which the guide wire 100 could be inserted, a maximum angle θ was recorded. When the maximum angle θ at which the guide wire 100 can be inserted is small, it can be said that prolapse is likely to occur. Therefore, among the side branches 220 into which the guide wire 100 could be inserted, in a case in which the maximum angle θ was θ≤100°, the evaluation was 'poor", in a case in which the angle θ was 100°<θ≤110°, the evaluation was "fair", and in a case in which the angle θ was 110°<θ≤120°, the evaluation was "good".

Kink Resistance Test

Figure 6:
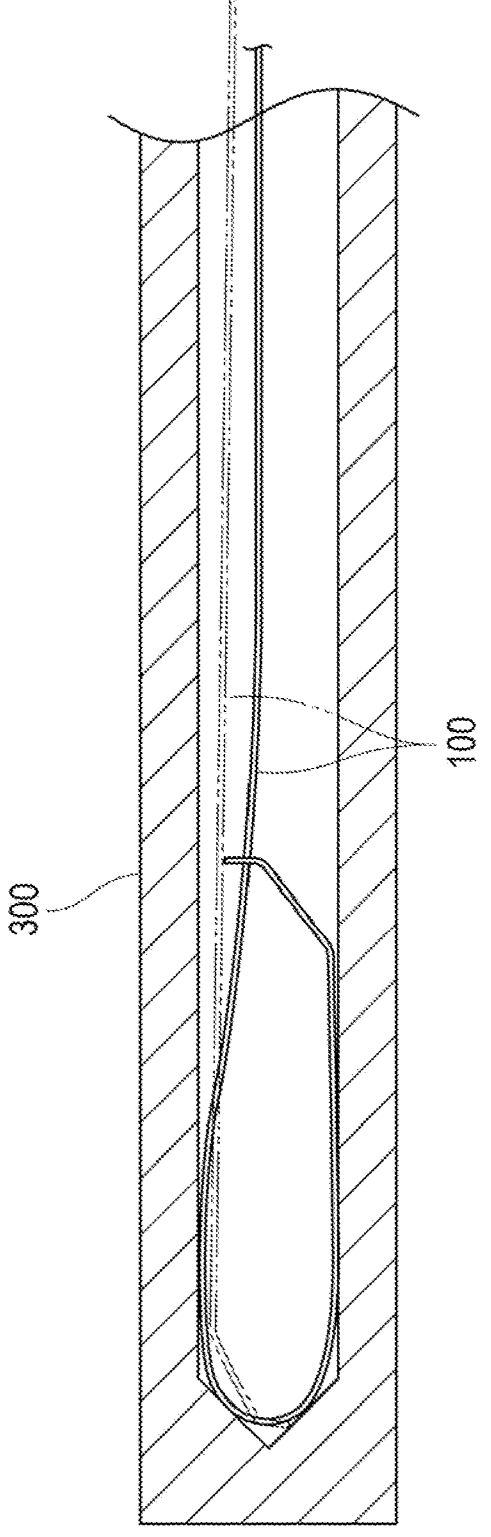
FIG. 6 is a schematic configuration diagram of a stenosis model used in a kink resistance test.
Figure 7:
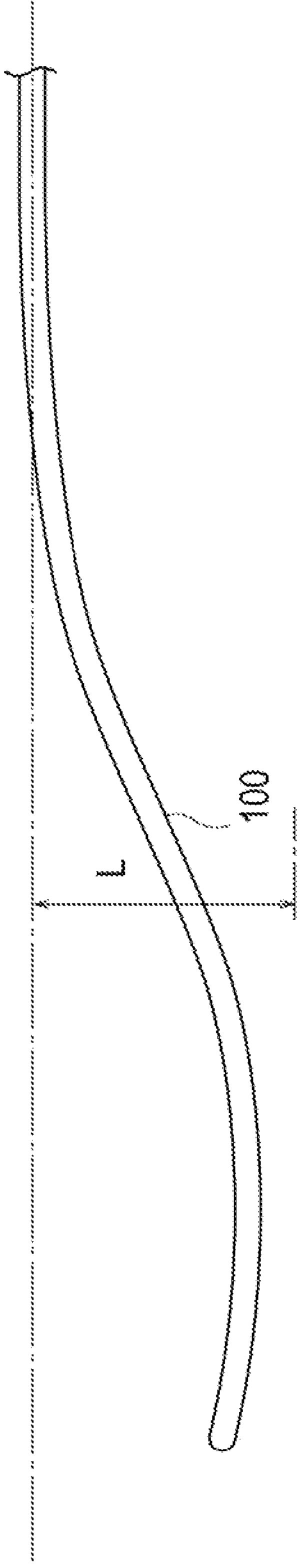
FIG. 7 is a diagram illustrating a bending height in the kink resistance test.

A kink resistance test was performed as follows. As illustrated in FIG. 6, a stenosis model 300 in which one end of a tube having an inner diameter of 2.5 mm was used as an occlusion end was prepared. The distal portion of the guide wire 100 was shaped into the shape illustrated in FIG. 5B. The distal end of the guide wire 100 was inserted from an opening of the stenosis model 300 filled with water, and came into contact with the occlusion end as in the guide wire 100 indicated by a two-dot chain line in FIG. 6. Next, the guide wire 100 was pushed 10 mm in the distal end direction while applying a torque, and the distal portion of the guide wire 100 was bent into a U-shape as in the guide wire 100 indicated by a solid line in FIG. 6. Thereafter, the guide wire 100 was pulled by 10 mm in the longitudinal direction to return to a state in which the distal portion was not bent in a U-shape. This operation was performed three times in total. The torque to the guide wire 100 was applied by a tester rotating the guide wire 100 once while holding the proximal portion of the guide wire 100. The guide wire 100 was removed from the stenosis model 300, and a bending height L of the guide wire 100 was confirmed with a digital microscope. As illustrated in FIG. 7, the "bending height L" refers to a length from the distal end of the guide wire 100 before shaping (in a linear state) to the distal end of the guide wire 100 after the kink resistance test on a plane passing through the central axis C of the guide wire 100 when the guide wire 100 is in a natural state. In a case in which the bending height L of the guide wire 100 after the kink resistance test was less than 4 mm, the evaluation was "good", and in a case in which the bending height L was 4 mm or more, the evaluation was "poor".

Evaluation Results

Table 3 (FIG. 10) shows evaluation results in Example 1 to Example 16, and Table 4 (FIG. 11) shows evaluation results in Comparative Example 1 to Comparative Example 4.

"ND" in the table means not measured.

Shaping Test and Shape Retaining Property Test

As illustrated in Table 3 (FIG. 10), the guide wires 100 in Example 1 to Example 16 have results of either "good" or "fair" in both the shaping property test and the shape retaining property test. The guide wires 100 in Example 1 to Example 16 have an elastic portion of total indentation work of the Ni—Ti alloy of the flat portion 11*g* of 46.0% to 59.5%, and have a Martens hardness of 1300 $N/mm^2$ to 3000 $N/mm^2$ (condition 1).

On the other hand, as illustrated in Table 4 (FIG. 11), the guide wires 100 in Comparative Example 1 to Comparative Example 4 have results of "poor" in either the shaping property test or the shape retaining property test. The guide wires 100 in Comparative Example 1 and Comparative Example 4 have results of "good" in the shaping property test, but have results of "poor" in the shape retaining property test. It is deduced that the guide wire 100 in Comparative Example 1 was unable to be shaped because the guide wire 100 has a Martens hardness larger than an upper limit value of condition 1 and is harder than those in Example 1 to Example 16. It is deduced that the guide wire 100 in Comparative Example 4 was unable to be shaped because the guide wire 100 has an elastic portion of total indentation work larger than the upper limit value of condition 1 and has a superelasticity higher than those in Example 1 to Example 16. Further, as illustrated in Table 4, the guide wires 100 in Comparative Example 2 and Comparative Example 3 have results of "good" in the shaping property test, but have results of "poor" in the shape retaining property test. It is deduced that the guide wire 100 in Comparative Example 2 was rather easily plastically deformed because the guide wire 100 has a Martens hardness smaller than a lower limit value of condition 1, and is softer than those in Example 1 to Example 16. It is deduced that the guide wire 100 in Comparative Example 3 was rather easily plastically deformed because the guide wire 100 has an elastic portion of total indentation work lower than the lower limit value of condition 1, and has a superelasticity lower than those in Example 1 to Example 16.

As described above, the guide wires 100 in which the flat portion 11*g* is formed of a Ni—Ti alloy satisfying condition 1 have both the shaping property and the shape retaining property.

Further, as illustrated in Table 3, the guide wires 100 in Example 1 to Example 3 has a result of "fair" in the shaping test, and the guide wires 100 in Example 4 to Example 16 has a result of "good" in the shaping test. The guide wires 100 in Example 4 to Example 16 have an elastic portion of total indentation work of the Ni—Ti alloy of the flat portion 11*g* of 46.0% to 59.5%, and have a Martens hardness of 1300 N/mm$^2$ to 2120 N/mm$^2$ (condition 2). It is deduced that the guide wires 100 in Example 1 to Example 3 were difficult to shape because the guide wires 100 have a Martens hardness larger than an upper limit value of condition 2 and are harder than the guide wires 100 in Example 4 to Example 16.

As described above, the guide wires 100 in which the flat portion 11*g* is formed of a Ni—Ti alloy satisfying condition 2 are more excellent in both the shaping property and the shape retaining property.

Prolapse Resistance Test

As illustrated in Table 3, the guide wires 100 in Example 1, Example 3 and Example 4, Example 6 to Example 8, and Example 11 to Example 16 have results of either "good" or "fair" in the prolapse resistance test. On the other hand, the guide wires 100 in Example 9 and Example 10 have results of "poor" in the prolapse resistance test. In each of the guide wires 100 in Example 1, Example 3 and Example 4, Example 6 to Example 8, and Example 11 to Example 16, the ratio of the length from the distal end of the transition portion 11*f* to the proximal end of the heat treatment region H along the longitudinal direction to the length of the transition portion 11*f* along the longitudinal direction (the heat treatment ratio) is 10% to 100% (condition 3). On the other hand, in each of the guide wires 100 in Example 9 and Example 10, the heat treatment ratio is smaller than a lower limit value of condition 3, and only a part of the flat portion 11*g* or only the flat portion 11*g* and a very small part of the distal end side of the transition portion 11*f* are subjected to the heat treatment. Therefore, as illustrated in FIG. 4B, it is deduced that the guide wires 100 in Example 9 and Example 10 have decreased prolapse resistance due to a sudden change in the rigidity occurred in a vicinity of the boundary between the flat portion 11*g* and the transition portion 11*f*.

Further, as illustrated in Table 3, the guide wires 100 in Example 4 and Example 6 to Example 8 have results of "good" in the prolapse resistance test. On the other hand, for example, the guide wires 100 in Example 12 and Example 13 have results of "fair" in the prolapse resistance test. In each of the guide wires 100 in Example 4 and Example 6 to Example 8, the ratio of the length from the distal end of the transition portion 11*f* to the proximal end of the heat treatment region H along the longitudinal direction to the length of the transition portion 11*f* along the longitudinal direction is 55% to 65% (condition 4). On the other hand, in the guide wire 100 in Example 12, the heat treatment ratio is smaller than a lower limit value of condition 4, and the proximal end of the heat treatment region H is disposed at the distal portion of the transition portion 11*f* having low rigidity. Therefore, it is deduced that the guide wire 100 in Example 12 has decreased prolapse resistance due to a sudden change in the rigidity occurred at the proximal end of the thermally treated region H. Further, in the guide wire 100 in Example 13, the heat treatment ratio is larger than an upper limit value of condition 4, and a length of the portion of the transition portion 11*f* where the rigidity is lower due to the heat treatment is long. Therefore, it is deduced that in the guide wire 100 in Example 13 has decreased prolapse resistance because it is difficult to transmit the pushing force to the distal end of the guide wire 100.

As described above, the guide wire 100 in which the ratio of the length from the distal end of the transition portion 11*f* to the proximal end of the heat treatment region H along the longitudinal direction to the length of the transition portion 11*f* along the longitudinal direction satisfies condition 3, and more preferably satisfies condition 4 is excellent in the prolapse resistance.

Kink Resistance Test

As illustrated in Table 3, the guide wires 100 in Example 1, Example 3 and Example 4, and Example 6 to Example 14 have results of "good" in the kink resistance test. On the other hand, the guide wires 100 in Example 15 and Example 16 have results of "poor" in the kink resistance test. In each of the guide wires 100 in Example 1, Example 3 and Example 4, and Example 6 to Example 14, the ratio of the length from the distal end of the transition portion 11*f* to the proximal end of the heat treatment region H along the longitudinal direction to the length of the transition portion 11*f* along the longitudinal direction is 10% or more and 100% or less (condition 3). On the other hand, in Example 15 and Example 16, the heat treatment ratio is larger than the upper limit value of condition 3, and even portions not subjected to cold working are subjected to heat treatment. Since the core component 10 is made of a Ni—Ti alloy, when a portion not subjected to cold working is subjected to heat treatment, the superelasticity is decreased, and plastic deformation is likely to occur. Therefore, it is deduced that the guide wires 100 in Example 15 and Example 16 have decreased kink resistance.

As described above, the guide wire 100 in which the heat treatment ratio in the transition portion 11*f* satisfies condition 3 is excellent in the kink resistance.

The detailed description above describes embodiments of a guide wire and a method of manufacturing a guide wire. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire, comprising:

an elongated core component including a flat portion at a distal end of the elongated core component;

the elongated core component includes, in an order from a distal end side, the flat portion, and a transition portion extending from a proximal end of the flat portion toward a proximal end side along a longitudinal direction;

the elongated core component includes a heat treatment region extending from a distal end of the flat portion to at least a part of the transition portion, the transition portion having a width and a thickness, and wherein the width of the transition portion increases toward the distal end side of the elongated core component along the longitudinal direction; and wherein the flat portion is made of a Ni—Ti alloy having an elastic portion of total indentation work of 46.0% to 59.5% and a Martens hardness of 1300 N/mm$^2$ to 3000 N/mm$^2$.

2. The guide wire according to claim 1, wherein the Martens hardness of the flat portion is 1300 N/mm$^2$ to 2120 N/mm$^2$.

3. The guide wire according to claim 1, wherein a ratio of a first length from a distal end of the transition portion to a proximal end of the heat treatment region along the longitudinal direction to a second length from the distal end of the transition portion to a proximal end of the transition portion along the longitudinal direction is 10% to 100%.

4. The guide wire according to claim 3, wherein the ratio of the first length from the distal end of the transition portion to the proximal end of the heat treatment region along the longitudinal direction to the second length from the distal end of the transition portion to the proximal end of the transition portion along the longitudinal direction is 55% to 65%.

5. The guide wire according to claim 1, wherein the elongated core component includes a first core member, the first core member extending from a proximal end of the elongated core component to the distal end side of the elongated core component includes a first bonding portion, a first constant outer diameter portion, a first tapered portion, a second constant outer diameter portion, the transition portion, and the flat portion.

6. The guide wire according to claim 5, wherein the first bonding portion is bonded to a second bonding portion of a second core member, and an outer diameter of the first bonding portion is larger than an outer diameter of the first constant outer diameter portion and is substantially equal to an outer diameter of the second bonding portion.

7. The guide wire according to claim 6, wherein the outer diameter of the first bonding portion and the outer diameter of the second bonding portion are larger than an outer diameter of the first constant outer diameter portion and an outer diameter of a proximal portion of the second core member.

8. The guide wire according to claim 1, wherein the flat portion has a rectangular transverse sectional shape.

9. The guide wire according to claim 8, wherein a thickness of the flat portion is substantially constant from a distal end of the transition portion to a distal end of the flat portion.

10. A guide wire, comprising:

an elongated core component including a flat portion at a distal end of the elongated core component, the flat portion having an elastic portion of total indentation work of 46.0% to 59.5% and a Martens hardness of 1300 N/mm$^2$ to 3000 N/mm$^2$;

the elongated core component includes, in an order from a distal end side, the flat portion, and a transition portion extending from a proximal end of the flat portion toward a proximal end side along a longitudinal direction;

the elongated core component includes a heat treatment region that includes an oxide film formed on an outer surface of the elongated core component extending from a distal end of the flat portion to at least a part of the transition portion along the longitudinal direction; and a tubular body that is spirally wound around a portion of the elongated core component and covers at least a portion of the oxide film formed on the outer surface of the elongated core component.

11. The guide wire according to claim 10, wherein the flat portion is made of a Ni—Ti alloy.

12. The guide wire according to claim 10, wherein the Martens hardness of the flat portion is 1300 N/mm$^2$ to 2120 N/mm$^2$.

13. The guide wire according to claim 10, wherein a ratio of a first length from a distal end of the transition portion to a proximal end of the heat treatment region along the longitudinal direction to a second length from the distal end of the transition portion to a proximal end of the transition portion along the longitudinal direction is 55% to 65%.

14. The guide wire according to claim 10, wherein the elongated core component includes a first core member, the first core member extending from a proximal end of the elongated core component to the distal end side of the elongated core component includes a first bonding portion, a first constant outer diameter portion, a first tapered portion, a second constant outer diameter portion, a transition portion, and the flat portion; and the tubular body includes a first coil and a second coil, the second coil being disposed on a proximal end side of the first coil, the first coil being disposed from the distal end of the first core member of elongated core component to an intermediate portion of the first core member of the elongated core component, and the second coil being disposed from the intermediate portion to a proximal end side of the first core member of the elongated core component.

15. The guide wire according to claim 5, further comprising:

a second tapered portion extending from a distal end of the second constant outer diameter to a proximal end of the transition portion, and wherein the thickness of the transition portion decreases from the second tapered portion toward the flat portion of the elongated core component along the longitudinal direction in a wedge shape.

16. The guide wire according to claim 1, wherein the width and the thickness of the transition portion are different.

17. A method of manufacturing a guide wire, the method comprising:

forming the guide wire according to claim 1, the forming of the guide wire including:

cold working the distal portion of the elongated core component such that the distal portion includes the flat portion and the transition portion extending from the proximal end of the flat portion toward the proximal end side along the longitudinal direction; and heat treating the flat portion and the at least a part of the transition portion such that the elastic portion of total indentation work of the flat portion is 46.0% to 59.5% and the Martens hardness of the flat portion is 1300 N/mm$^2$ to 3000 N/mm$^2$.

18. The method according to claim 17, wherein the Martens hardness of the flat portion is 1300 N/mm$^2$ to 2120 N/mm$^2$.

19. The method according to claim 17, wherein a ratio of a first length from a distal end of the transition portion to a proximal end of the heat treatment region along the longitudinal direction to a second length from the distal end of the transition portion to a proximal end of the transition portion along the longitudinal direction is 10% to 100%.

20. The method according to claim 19, wherein the ratio of the first length from the distal end of the transition portion to the proximal end of the heat treatment region along the longitudinal direction to the second length from the distal end of the transition portion to the proximal end of the transition portion along the longitudinal direction is 55% to 65%.

* * * * *